US006590107B1

(12) United States Patent
Schinazi et al.

(10) Patent No.: US 6,590,107 B1
(45) Date of Patent: Jul. 8, 2003

(54) SYNTHESIS, ANTI-HUMAN IMMUNODEFICIENCY VIRUS, AND ANTI-HEPATITIS B VIRUS ACTIVITIES OF 1,3-OXASELENOLANE NUCLEOSIDES

(75) Inventors: Raymond F. Schinazi, Decatur, GA (US); Chung K. Chu, Athens, GA (US); Jinfa Du, Irvine, CA (US)

(73) Assignees: Emory University, Atlanta, GA (US); The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/799,327

(22) Filed: Mar. 5, 2001

Related U.S. Application Data

(60) Continuation of application No. 09/517,955, filed on Mar. 3, 2000, now Pat. No. 6,197,777, which is a division of application No. 09/044,558, filed on Mar. 19, 1998, now Pat. No. 6,071,922.

(60) Provisional application No. 60/041,265, filed on Mar. 19, 1997.

(51) Int. Cl.[7] .............................. C07F 9/28; C07F 9/22; C07H 19/20; C07D 473/00; C07D 239/02

(52) U.S. Cl. ...................... 549/222; 549/216; 549/218; 536/26.7; 544/244; 544/264; 544/265; 544/317

(58) Field of Search ................................ 549/216, 218, 549/222; 536/26.7; 544/244, 264, 265, 317

(56) References Cited

U.S. PATENT DOCUMENTS

| | | | |
|---|---|---|---|
| 5,041,449 A | 8/1991 | Belleau | 514/274 |
| 5,047,407 A | 9/1991 | Belleau | 514/274 |
| 5,149,794 A | 9/1992 | Yatvin et al. | 536/29 |
| 5,194,654 A | 3/1993 | Hostetler et al. | 558/152 |
| 5,204,466 A | 4/1993 | Liotta et al. | 544/317 |
| 5,210,085 A | 5/1993 | Liotta et al. | 514/274 |
| 5,223,263 A | 6/1993 | Hostetler et al. | 424/450 |
| 5,256,641 A | 10/1993 | Yatvin | 514/2 |
| 5,463,092 A | 10/1995 | Hostetler | 554/40 |

(List continued on next page.)

FOREIGN PATENT DOCUMENTS

| | | |
|---|---|---|
| EP | 0 328 526 A | 8/1990 |
| EP | 0 337 713 B1 | 10/1995 |
| WO | WO91/09124 | 6/1991 |
| WO | WO 91/11186 | 8/1991 |
| WO | WO 92/10496 | 6/1992 |
| WO | WO 92/10497 | 6/1992 |
| WO | WO 92/14743 | 9/1992 |
| WO | WO 94/04154 | 3/1994 |

OTHER PUBLICATIONS

Sastry, J.K., et al., Membrane–permeable dideoxyuridine 5'–monophosphate analogue inhibits human immunodeficiency virus infection. Mol. Pharmacol. 41, 441–445; (1992).

(List continued on next page.)

Primary Examiner—Richard L. Raymond
Assistant Examiner—Tamthom N. Truong
(74) Attorney, Agent, or Firm—King & Spalding LLP; Sherry M. Knowles, Esq.

(57) ABSTRACT

A method and composition for the treatment of HIV infection, HBV infection, or abnormal cellular proliferation in humans and other host animals is disclosed that includes the administration of an effective amount of a 1,3-oxaselenolane nucleoside or a pharmaceutically acceptable salt thereof, optionally in a pharmaceutically acceptable carrier.

13 Claims, 4 Drawing Sheets

U.S. PATENT DOCUMENTS

| | | | |
|---|---|---|---|
| 5,466,806 A | 11/1995 | Belleau et al. | 544/310 |
| 5,486,520 A | 1/1996 | Belleau et al. | 514/274 |
| 5,538,975 A | 7/1996 | Dionne | 514/256 |
| 5,539,116 A | 7/1996 | Liotta | 544/317 |
| 5,543,389 A | 8/1996 | Yatvin | 514/2 |
| 5,543,390 A | 8/1996 | Yatvin | 514/2 |
| 5,543,391 A | 8/1996 | Yatvin | 514/2 |
| 5,554,728 A | 9/1996 | Basava et al. | 530/327 |
| 5,618,820 A | 4/1997 | Dionne | 514/274 |
| 5,700,937 A | 12/1997 | Liotta et al. | 544/317 |
| 5,728,575 A | 3/1998 | Liotta et al. | 435/280 |
| 5,814,639 A | 9/1998 | Liotta et al. | 514/274 |
| 5,827,727 A | 10/1998 | Liotta et al. | 435/280 |
| 5,892,025 A | 4/1999 | Liotta et al. | 536/46 |
| 5,914,331 A | 6/1999 | Liotta et al. | 514/274 |
| 5,914,400 A | 6/1999 | Liotta et al. | 544/314 |

OTHER PUBLICATIONS

Schinazi, et al., Selective Inhibition of Human Immunodeficiency Viruses by Racemates and Enantiomers of cis–5–Fluoro–1–[2–(Hydroxymethyl)–1, 3–Oxathiolane–5–yl] Cytosine, Antimicrobial Agents and Chemotherapy,36 (11), 2423–2432 (1992).

Schinazi, et al., Antimicrob. Agents Chemother. 32, 1784–1787 (1988).

Schinazi, et al., Antimicrob. Agents Chemother. 34:1061–1067 (1990).

Schinazi, et al., Effect of Combinations of Acylovir with Vidarabine or its 'Monophosphate on Herpes Simplex Viruses in Cell Culture and in Mice, Antimicrobial Agents and Chemotherapy, 22 (3), 499, (1982).

Schinazi, et al., Mutations in retroviral genes associated with drug resistance, International Antiviral News, vol. 1(6), International Medical Press(1996).

Shuto, S., et al., A facile one–step synthesis of 5'–phosphatidylnucleosides by an enzymatic two–phase reaction. Tetrahedron Lett. 28, 199–202; (1987).

Nargeot, J. et al., Time course of the increase in the myocardial slow inward current after a photochemically generated concentration jump of intraceluar cAMP, Natl. Acad. Sci. U.S.A. 80, 2395–2399; (1983).

Norbeck, Tetrahedron Letters 30 (46), 6246 (1989).

Ohno, R., et al., Treatment of myelodyspastic syndromes with orally administered 1–β–D–rabinofuranosylcytosine–5'–stearylphosphate. Oncology 48, 451–455 (1991).

Palomino, E., et al., A dihydropyridine carrier system for sustained delivery of 2',3'dideoxynucleosides to the brain., J. Med. Chem. 32, 622–625; (1989).

Philpott, M.S., et al., Evaluation of 9–(2–phosphonylmethoxyethyl) adenine therapy for feline immunodeficiency virus using a quantitative polymerase chain reaction, Vet. Immunol. Immunopathol. 35:155–166, (1992).

Piantadosi, C., et al. (1991) Synthesis and evaluation of novel ether lipid nucleoside conjugates for anti–HIV–1 activity. J. Med. Chem. 34, 1408–1414.

Prisbe, E.J., et al. (1986) Synthesis and antiherpes virus activity of phosphate and phosphonate derivatives of 9–[(1, 3–dihydroxy–2–propoxy)methyl] guanine. J. Med. Chem. 29, 671–675.

Puech, F., et al. (1993) Intracellular delivery of nucleoside monophosphate through a reductase–mediated activation process. Antiviral Res. 22, 155–174.

Rosowsky, A., et al., Lipophilic 5'–(alkylphosphate) esters of 1–β–D–arabinofuranosylcytosine and its N4–acyl and 2.2'–anhydro–3'0–acyl derivatives as potential prodrugs. J. Med. Chem. 25, 171–178; (1982).

Ryu, E.K., et al., Phospholipid–nucleoside conjugates 3. Synthesis and preliminary biological evaluation of 1–β–D–arabinofuranosylcytosine 5'diphosphate[–], 2–diacylglycerols. J. Med. Chem. 25, 1322–1329; (1982).

Saffhill, R. et al., The degradation of 5–iododeoxyurindine and 5–bromoeoxyuridine by serum from different sources and its consequences for the use of these compounds for incorporation into DNA. Chem. Biol. Interact. 57, 347–355; (1986).

Korba et al., "A cell culture assay for compounds which inhibit hepatitis B virus replication," Antiviral Res., 15:217 1991.

Kumar, et al. Synthesis and biological evaluation of some cyclic phosphoramidate nucleoside derivatives. J. Med. Chem. 33, 2368–2375 (1990).

Lebec, C., et al. Synthesis of lipophilic phosphate triester derivatives of 5–fluorouridine and arabinocytidine as anticancer prodrugs, Tetrahedron Lett. 32, 6553–6556 (1991).

Lichtenstein, J. et al. The metabolism of exogenously supplied nucleotides by *Escherichia coli.*, J. Biol. Chem. 235, 457–465; (1960).

McDougal, et al., Immunoassay for the Detection and Quanititation of Infectious Human Retrovirus. Lymphadenopathy–Associated Virus (LAV), J. Immun. Meth. 76, 171–183, (1985).

McGuigan, C. et al., Synthesis and biological evaluation of some phosphate triester derivatives of the anti–viral drug Ara. Nucleic Acids Res. 17, 6065–6075; (1989).

McGuigan, C., et al., Synthesis and anti–HIV activity of some novel substituted dialkyl phosphate derivatives of AZT and ddCyd., Antiviral Chem. Chemother. 1:355–360 (1990b).

McGuigan, C., et al. Intracellular delivery of bioactive AZT nucleotides by aryl phosphate derivatives of AZT. J. Med. Chem. 36, 1048–1052 (1993b).

McGuigan, C., et al., Phosphoramidate derivatives of AZT as inhibitors of HIV; studies on the caroxyl terminus. Antiviral Chem. Chemother. 4, 97–101; (1993a).

McGuigan, C., et al., Aryl phosphate derivatives of AZT retain activity against HIV1 in cell lines which are resistant to the action of AZT. Antiviral Res. 17, 311–321 (1992).

Meyer, R.B., Jr., et al., Synthesis of purine nucleoside 3',5'–cyclic phosphoramidates. Tetrahedron Lett., 269–272; (1973).

Namane, A., et al. (1992) Improved brain delivery of AZT using a glycosyl phosphotriester prodrug. J. Med. Chem. 35, 3939–3044.

Ho, "Distribution of Kinase and Deaminase of 1–D–arabinofuranosylcytosine in tissues of man and mouse," Cancer Res., 33:2816–2820 (1973).

Hoard et al., "Conversion of Mono– and Oligodeoxyribonucleotides to 5'–Triphosphates," J. Am. Chem. Soc., 87(8):1785–1788 (1965).

Hong et al., "Synthesis and Antitumor Activity of 1,3–Arabinofuranosylcytosine Conjugates or Cortisol and Cortisone," Biochem. Biophys. Rs. Commun., 88:1223–1229 (1979).

Hong, C.I., et al. (1980) Nucleoside conjugates. 6. Synthesis and comparison of antitumor activity of 1-(β-D-arabinofuranosyl) cytosine conjugates of corticosteroids and selected lipophilic alcohols. J. Med. Chem. 28, 171–177.

Hostetler et al., "Phosphatidylazidothymidine and phosphatidyl–ddC: Assessment of uptake in mouse lymphoid tissues and antiviral activities in human immunodeficiency virus–infected cells and in raushcher leukemia virus–infected mice." Antimicrobial Agents Chemother. 38 (12):2792–2797; (1994).

Hostetler, K.Y., et al. Antiviral activity of phosphatidyl–dideoxycytidine in hepatitis B–infected cells and enhanced hepatic uptake in mice. Antiviral Res. 24:59–67; (1994).

Ji, Y.H., Monophosphoric Acid Diesters of 7β–Hydroxycholesterol and of Pyrimidine Nucleosides as Potential Antitumor Agents: Synthesis and preliminary Evaluation of Antitumor Activity, J. Med Chem., 33,2264–2270, (1990).

Jones, et al., Mini Review: Nucleotide prodrugs, Antiviral Research, 27, 1–17 (1995).

Kataoka et al. "A convenient synthesis of adenosine 3',5' cyclic phosphate (cAMP) benzyl and methyl triesters." Heterocycles 32:1351–1356 (1991).

Kinchington et al. "Comparison of antiviral effects of zidovudine phosphoramidate and phosphorodiamidate derivatives against HIV and ULV in vitro," Antiviral Chem. Chemother. 3, 107–112 (1992).

Kodama, et al., "Antitumor activity and pharmacology of 1–β–D–arabinofuranosylcytosine–5'–stearylphosphate; an orally active derivative of 1–β–D–arabinofuranosylcytosine," J. Cancer Res. 80, 679–685; (1989).

Chang et al., "Deoxycytidine Deaminase–resistant Stereoisomer is the Active From of (–)–2',3'–thia–cytidine in the Inhibition of Hepatitis B Virus Replication," J. Biol. Chem., 267(20):13938–13942 (1992).

Davisson et al., "Synthesis of Nucleotide 5'–Diphosphates from 5'–O–Tosyl Nucleosides," J. Org. Chem., 52(9):1794–18081 (1987).

Du et al., "Synthesis, Anti–Human Immunodeficiency Virus and Anti–Hepatitis B Virus Activities of Novel Oxaselenolane Nucleosides," J. Med. Chem., 40(19):2991–2993 (1997).

Furman, et al., "The Anti–Hepatitis B Virus Activities, Cytotoxicities, and Anabolic Profiles of the (–) and (+) Enantiomers of cis–5–Fluoro–1–[2–(Hydroxymethyl)–1, 3–oxathiolane–5–yl]–Cytosine," Antimicrob. Agents and Chemother., 36(12):2686–2692 (1992).

$^a$R=(-)-L-menthyl; (a) LiAl[OC(CH$_3$)$_3$]$_3$H, THF, -10°C; (b) Ac$_2$O; (c) (i) 2,4,6-collidine, (CH$_3$)$_3$CSi(CH$_3$)$_2$OSO$_2$CF$_3$, 5FCyt, CH$_2$Cl$_2$; (ii)(CH$_3$)$_3$CSiI, 20°C; (d): LiAlH$_4$, THF, 20°C (+)-β-Se-ddC            (−)-β-Se-ddC (+)-β-Se-FddC            (−)-β-Se-FddC

SYNTHESIS, ANTI-HUMAN IMMUNODEFICIENCY VIRUS, AND ANTI-HEPATITIS B VIRUS ACTIVITIES OF 1,3-OXASELENOLANE NUCLEOSIDES This application is a continuation application of U.S. patent application Ser. No. 09/517,955, now granted as U.S. Pat. No. 6,197,777, filed on Mar. 3, 2000, which is a divisional application of U.S. patent application Ser. No. 09/044,558, now granted as U.S. Pat. No. 6,071,922, filed on Mar. 19, 1998, which claims priority to U.S. provisional application No. 60/041,265, filed on Mar. 19, 1997, all filed by Raymond F. Schinazi, Chung K. Chu, and Jinfa Du.

The U.S. government has rights in this invention resulting from U.S. Public Health Service Research grants from the National Institute of Allergy and Infectious Diseases and the Department of Veterans Affairs which partially funded the research leading to this invention.

BACKGROUND OF THE INVENTION

This invention is in the area of synthetic nucleosides, and is specifically directed to 1,3-oxaselenolane nucleosides and their pharmaceutical uses, compositions, and method of preparation.

In 1981, acquired immune deficiency syndrome (AIDS) was identified as a disease that severely compromises the human immune system, and that almost without exception led to death. In 1983, the etiological cause of AIDS was determined to be the human immunodeficiency virus (HIV).

In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), 2',3'-dideoxy-2',3'-didehydrothymidine (D4T), and (1S,4R)-4-[2-amino-6-cyclopropyl-amino)-9H-purin-9-yl]-2-cyclopentene-1-methanol succinate ("159U89"), have been proven to be effective against HIV. In general, after cellular phosphorylation to the 5'-triphosphate by cellular kinases, these synthetic nucleosides are incorporated into a growing strand of viral DNA, causing chain termination due to the absence of the 3'-hydroxyl group. They can also or alternatively inhibit the viral enzyme reverse transcriptase or DNA polymerase.

The success of various synthetic nucleosides in inhibiting the replication of HIV in vivo or in vitro has led a number of researchers to design and test nucleosides that substitute a heteroatom for the carbon atom at the 3'-position of the nucleoside. Norbeck, et al., disclosed that (±)-1-[(2β,4β)-2-(hycroxymethyl)-4-dioxolanyl]thymine (referred to as (±)-dioxolane-T) exhibits a modest activity against HIV ($EC_{50}$ of 20 $\mu$M in ATH8 cells), and is not toxic to uninfected control cells at a concentration of 200 $\mu$M. *Tetrahedron Letters* 30 (46), 6246, (1989). European Patent Application Publication No. 0 337 713 and U.S. Pat. No. 5,041,449, assigned to BioChem Pharma, Inc., disclose racemic 2-substituted-4-substituted-1,3-dioxolanes that exhibit antiviral activity. Published PCT applications PCT/US91/09124 and PCT/US93/08044 disclose purified β-D-1,3-dioxolanyl nucleosides for the treatment of HIV infection. PCT discloses the use of purified β-D-1,3-dioxolanyl nucleosides for the treatment of HBV infection.

PCT/US95/11464 discloses that (−)-(2S,4S)-1-(2-hydroxymethyl-1,3-dioxolan-4-yl)cytosine is useful in the treatment of tumors and other abnormal cell proliferation.

U.S. Pat. No. 5,047,407 and European Pat. Application Publication No. 0 382 526, both to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the same activity against HIV as AZT, with less toxicity. U.S. Pat. No. 5,539,116 to Liotta, et al is directed to the (−)-enantiomer of BCH-189, known as 3TC, is now sold commercially for the treatment of HIV in humans in the United States.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]Cytosine" *Antimicrobial Agents and Chemotherapy,* November 1992, page 2423–2431. See also U.S. Pat. Nos. 5,210,085; 5,204,466, WO 91/11186, and WO 92/14743.

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized coutrines, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. See Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy,* December 1992, page 2686–2692; and Cheng, et al., *Journal of Biological Chemistry,* Volume 267(20), 13938–13942 (1992).

A human serum-derived vaccine has been developed to immunize patients against HBV. However, more recently, vaccines have also been produced through genetic engineering and are currently used widely. Unfortunately, vaccines cannot help those already infected with HBV. Daily treatment with α-interferon, a genetically engineered protein, has also shown promise, but this therapy is only successful in about one third of treated patients. Further, interferon cannot be given orally.

Since 1,3-doxolane and 1,3-oxathiolane nucleosides have exhibited promising antiviral and anticancer activities, it was of interest to synthesize an isosteric class of compounds, 1,3-oxaselenolane nucleosides in search of biologically interesting nucleosides. Despite their structural similarity to the 3'-heteroatom substituted nucleosides, the synthesis of 1,3-oxaselenolane nucleosides has been elusive as the construction of the oxaselenolane ring is difficult. For this reason, it appears that 1,3-oxaselenolane nucleosides have never been reported.

In light of the fact that acquired immune deficiency syndrome, AIDS-related complex, and hepatitis B virus have reached epidemic levels worldwide, and have tragic effects on the infected patient, there remains a strong need to provide new effective pharmaceutical agents to treat these diseases.

Therefore, it is an object of the present invention to provide a method and composition for the treatment of human patients infected with HIV.

It is another object of the present invention to provide a method and composition for the treatment of human patients or other host animals infected with HBV.

It is a further object of the invention to provide a method for the synthesis of 1,3-oxaselenolanyl nucleosides.

It is a still further object of the invention to provide 1,3-oxaselenolanyl nucleosides and pharmaceutical compositions that include 1,3-oxaselenolanyl nucleosides.

SUMMARY OF THE INVENTION

A method and composition for the treatment of HIV or HBV infection in humans and other host animals is disclosed that includes the administration of an effective amount of a 1,3-oxaselenolane nucleoside or a pharmaceutically acceptable salt thereof, optionally in a pharmaceutically acceptable carrier.

In one embodiment, the 1,3-oxaselenolane nucleoside has the formula:

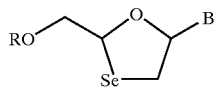

wherein B is a purine or pyrimidine base, and R is hydrogen, acyl or a phosphate ester, including monophosphate, diphosphate, or triphosphate. In another embodiment, the 1,3-oxaselenolanyl nucleoside is provided as a lipophilic or hydrophilic prodrug as discussed in more detail below. In another alternative embodiment, the selenium atom is oxidized in the molecule. Preferred 1,3-oxaselenolanyl nucleosides are those that exhibit an activity against HIV or HBV at a concentration of not greater than approximately 5 micromolar, and most preferably approximately 1 micromolar or less in an in vitro assay such as those described in detail in this application. For treatment of HIV and HBV, it is also preferred that the 1,3-oxaselenolanyl nucleoside exhibit an $IC_{50}$ toxicity in an in vitro assay such as those described herein of greater than 50 micromolar, and more preferably, approximately 100 micromolar or greater.

The 1,3-oxaselenolane nucleoside is preferably either a β-L-nucleoside or a β-D-nucleoside, as an isolated enantiomer. In one embodiment, the nucleoside is a β-L- or β-D-nucleoside in substantially pure form, i.e., substantially in the absence of the corresponding β-D- or β-L-nucleoside.

Preferred compounds are 2-hydroxymethyl-4-(N-5'-cytosin-1'-yl)-1,3-oxaselenolane and 2-hydroxymethyl-4-(N-5'-fluorocytosin-1'-yl)-1,3-oxaselenolane. It has been discovered that the isolated (−)-β-L-enantiomer of these nucleosides are more potent than their β-D counterparts. The (+)-enantiomers of these compounds, however, are not toxic to CEM cells.

In another embodiment, the active compound or its derivative or salt can be administered in combination or alternation with another antiviral agent, such as an other anti-HIV agent or anti-HBV agent, as described in more detail in Section IV. In general, during alternation therapy, an effective dosage of each agent is administered serially, whereas in combination therapy, an effective dosage of two or more agents are administered together. The dosages will depend on absorption, inactivation, and excretion rates of the drug as well as other factors known to those of skill in the art. It is to be noted that dosage values will also vary with the severity of the condition to be alleviated. It is to be farther understood that for any particular subject, specific dosage regimens and schedules should be adjusted over time according to the individual need and the professional judgment of the person administering or supervising the administration of the compositions.

The compounds can also be used to treat equine infectious anemia virus (EIAV), feline immunodeficiency virus, and simian immunodeficiency virus. (Wang, S., Montelaro, R., Schinazi, R. R., Jagerski, B. and Mellors, J. W.: Activity of nucleoside and non-nucleoside reverse transcriptase inhibitors (NNRTI) against equine infectious anemia virus (EIAV). First National Conference on Human Retroviruses and Related Infections, Washington, D.C., Dec. 12–16, 1993; Sellon D. C., Equine Infectious Anemia, Vet Clin. North Am. Equine Pract. United States, 9: 321–336, 1993; Philpott, M. S., Ebner, J. P., Hoover, E. A., Evaluation of 9-(2-phosphonylmethoxyethyl)adenine therapy for feline immunnodeficiency virus using a quantitative polymerase chain reaction, Vet. Inumunol. Immunopathol. 35:155166, 1992.)

DETAILED DESCRIPTION OF THE INVENTION

Figure 1:
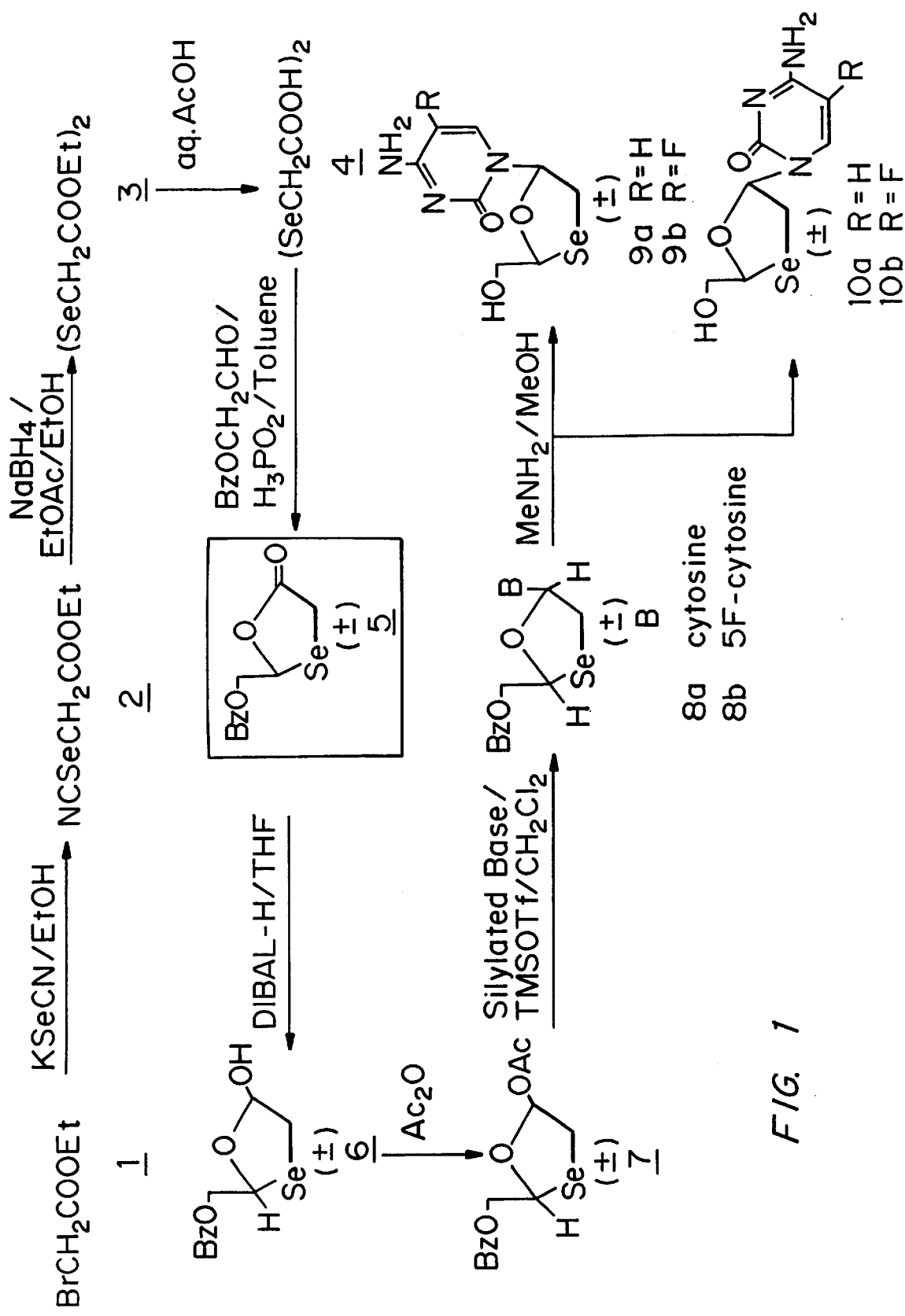
FIG. 1 is an illustration of one process for the preparation of a 1,3-oxaselenolanyl nucleoside according to the present invention, as described in Example 1.

As used herein, the term "isolated enantiomer" refers to a nucleoside composition that includes at least approximately 95% to 100%, or more preferably, over 97% of a single enantiomer of that nucleoside.

The term "substantially pure form" refers to a nucleoside composition of one enantiomer that includes no more than about 5% w/w of the other enantiomer, more preferably no more than about 2%, and most preferably less than about 1% w/w is present The term purine or pyrimidine base, includes, but is not limited to, $N^6$-alylpurines, $N^6$-acylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^4$-alkylpyrimidines, $N^4$-acylpyrimidines, $N^4$-benzylpurine, $N^4$-halopyrimidines, $N^4$-vinylpyrimidines, $N^4$-acetylenic pyriridines, $N^4$-acyl pyrimidines, $N^4$-hydroxyalkyl pyrinidines, $N^6$-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimdine, $N^2$-alkylpurines, $N^2$-alkyl-6-thiopurines, 5-azacytidinyl, 5-azauracilyl, trazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and included trimethylsilyl, dimethylhexylsilyl, t-butyldimenthylsilyl, and t-butyldiphenylsilyl, trityl, alkyl groups, acyl groups such as acetyl and propionyl, methanesulfonyl, and p-toluenesulfonyl. Preferred bases include cytosine, 5-fluorocytosine, uracil, thymine, adenine, guanine, xanthine, 2,6-diaminopurine, 6-aminopurine, and 6-chloropurine.

The term alkyl, as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John wiley and Sons, Second Edition, 1991, hereby incorporated by reference.

The term lower alkyl, as used herein, and unless otherwise specified, refers to a $C_1$ to $C_4$ saturated straight or branched alkyl group.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The aryl group can be optionally substituted with one or more moieties selected from the group consisting of hydroxyl, halo, alkyl, alkenyl, alkynyl, alkaryl aralkyl, amino, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term acyl refers to moiety of the formula —C(O)R', wherein R' is alkyl, aryl, alkaryl, aralkyl, heteroaromatic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

As used herein, a leaving group means a functional group that is cleaved from the molecule to which it is attached under appropriate conditions.

The term amino acid includes naturally occurring and synthetic amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxantinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, 1-butyldimethylsilyl, and t-butyldiphenylsilyl, trityl or substituted trityl, alkyl groups, acycl groups such as acetyl and propionyl, methanesulfonyl, and p-toluenelsulfonyl.

The term lipophilic prodrug refers to a 1,3-oxaselenolanyl nucleoside that contains a covalent substituent that is cleavable at the 5'-hydroxyl position that renders the nucleoside more lipophilic than the parent nucleoside with a 5'-hydroxyl group.

The term hydrophilic prodrug refers to a 1,3-oxaselenolanyl nucleoside that contains a covalent substitutent at the 5'-hydroxyl position that renders the nucleoside more hydrophilic than the parent nucleoside with a 5'-hydroxyl group.

The invention as disclosed herein is a method and composition for the treatment of HIV or HBV infection, and other viruses infections replicating in like manner, in humans or other host animals, that includes administering an effective amount of a 1,3-oxaselenolanyl nucleoside, a pharmaceutically acceptable derivative thereof, including a 1,3-oxaselenolanyl nucleoside with a 5' leaving group, including an acylated or phosphorylated derivative or a pharmaceutically acceptable salt thereof, optionally in a pharmaceutically acceptable carrier. The compounds of this invention either possess antiviral activity, such as anti-HIV-1, anti-HIV-2, anti-HBV, or anti-simian immunodeficiency virus (anti-SIV) activity themselves or are metabolized to a compound that exhibits antiviral activity.

The disclosed compounds or their pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

The compound or its pharmaceutically acceptable derivatives or salt, or pharmaceutically acceptable formulations containing the compound or its derivatives or salt, are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV antigen positive or who have been exposed to HBV.

The compound can be converted into a pharmaceutically acceptable ester by reaction with an appropriate esteriig agents, for example, an acid halide or anhydride. The compound or its pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

In summary, the present invention, includes the following features:

(a) 1,3-oxaselenolane nucleosides as outlined above, and pharmaceutically acceptable derivatives and salts thereof;

(b) 1,3-oxaselenolane nucleosides, and pharmaceutically acceptable derivatives and salts thereof for use in medical therapy, for example for the treatment or prophylaxis of an HIV or HBV infection;

(c) use of 1,3-oxaselenolane nucleosides and pharmaceutically acceptable derivatives and salts thereof in the manufacture of a medicament for treatment of an HIV or HBV infection;

(d) pharmaceutical formulations comprising 1,3-oxaselenolane nucleosides or a pharmaceutically acceptable derivative or salt thereof together with a pharmaceutically acceptable carrier or diluent;

(e) processes for the preparation of 1,3-oxaselenolane nucleosides; and (f) use of 1,3-oxaselenolanyl nucleosides in the treatment of viral infections by administration in combination or alternation with another antiviral agent.

I. Active Compound, and Physiological Acceptable Derivatives and Salts Thereof

The active compounds disclosed herein are 1,3-oxaselenolane nucleosides, in the racemic form or as isolated enantiomers.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and the 5' and $N^4$ pyrimidine or $N^6$-purine acylated or alkylated derivatives of the active compound (alternatively referred to as "physiologically active derivatives"). In one embodiment, the acyl group is a carboxylic acid ester in which the noncabonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, phosphate, including but not limited to mono, di or triphosphate ester, trityl or monomethoxytrityl, substituted benzyl, trialkylsilyl (e.g., dimethyl-5-butylsilyl) or diphenylmethylsilyl. Aryl groups in the esters optionally comprise a phenyl group.

Modifications of the active compound, and especially at the $N^4$ pyrimidinyl or $N^6$ purine and 5'-O positions, can affect the bioavailability and rate of metabolism of the active species, thus providing control over the delivery of the active species. Further, the modifications can affect that antiviral activity of the compound, in some cases increasing the activity over the parent compound. This can easily be assessed by preparing the derivative and testing its antiviral activity according to the methods described herein, or other methods known to those skilled in the art.

Nucleotide Prodrugs

Any of the nucleotides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research,* 27 (1995) 1–17. Any of these can be used in combination with the disclosed nucleosides to achieve a desired effect.

In one embodiment, the 1,3-oxaselenolanyl nucleoside is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin, et al.); U.S. Pat. No. 5,194,654 (Mar. 16, 1993, Hostetler, et al.); U.S. Pat. No. 5,223,263 (Jun. 29, 1993, Hostetler, et al.); U.S. Pat. No. 5,256,641 (Oct. 26, 1993, Yatvin, et al.); U.S. Pat. No. 5,411,947 (May 2, 1995, Hostetler, et al.); U.S. Pat. No. 5,463,092 (Oct. 31, 1995, Hostetler, et al.); U.S. Pat. No. 5,543,389 (Aug. 6, 1996, Yatvin, et al.); U.S. Pat. No. 5,543,390 (Aug. 6, 1996, Yatvin, et al.); U.S. Pat. No. 5,543,391 (Aug. 6, 1996, Yatvin, et al.); and U.S. Pat. No. 5,554,728 (Sep. 10, 1996, Basava, et al.), all of which are incorporated herein by reference.

Foreign patent applications that disclose lipophilic substituents that can be attached to the 1,3-oxaselenolanyl nucleosides of the present invention, or lipophilic preparations, include WO 89/02733, WO 90/00555, WO 91/16920, WO 91/18914, WO 93/00910, WO 94/26273, WO/15132, EP 0 350 287, EP 93917054.4, and WO 91/19721.

Additional nonlimiting examples of derivatives of 1,3-oxaselenolanyl nucleosides are those that contain substituents as described in the following publications. These derivatized 1,3-oxaselenolanyl nucleosides can be used for the indications described in the text or otherwise as antiviral agents, including as anti-HIV or anti-HBV agents. Ho, D. H. W. (1973) Distribution of Kinase and deaminase of 1β-D-arabinofuranosylcytosine in tissues of man and mouse. *Cancer Res.* 33, 2816–2820; Holy, A. (1993) Isopolar phosphorous-modified nucleotide analogues. In: De Clercq (ed.), Advances in Antiviral Drug Design, Vol. I, JAI Press, pp. 179–231; Hong, C. I., Nechaev, A., and West C. R. (1979a) Synthesis and antitumor activity of 1β-3- arabinofuranosylcytosine conjugates of cortisol and cortisone. *Biochem Biopsis. Rs. Commun.* 88, 1223–1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(β-D-arabinofuranosyl)cytosine conjugates of corticosteriods and selected lipophilic alcohols. *J. Med Chem.* 28, 171–177; Hostetler, K. Y., Stuhmiller, L. M., Lenting, H. B. M. van den Bosch, H. and Richman, D. D. (1990) Synthesis and antiretroviral activity of phospholipid analogs of azidothymidine and other antiviral nucleosides. *J. Biol. Chem.* 266, 11714–11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. *Antiviral Res.* 24, 59–67; Hostetler, K. Y., Richman, D. D., Sridhar, C. N. Feigner, P. L., Feigner, J., Ricci, J., Gerdener, M. F. Sellese, D. W. and Ellis, M. N. (1994b) Phosphatidylazidothymidine and phosphatidyl-ddC: Assessment of uptake in mouse lymphoid tissues and antiviral activities in human immunodeficiency virus-infected cells and in rauseher leukemia virus-infected mice. *Antimicrobial Agents Chemother.* 38, 2792–2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27, 440–444; Ji, Y. H., Moog, C., Schmitt, G., Bischoff, P. and Luu, B. (1990); Monophosphoric acid diesters of 7β-hydroxycholesterol and of pyrimidine nucleosides as potential antitumor agents; synthesis and preliminary evaluation of antitumor activity. *J. Med. Chem.* 33, 2264–2270; Jones, A. S., McGuigan, C., Walter, R. T., Balzarini, J. and DeClercq, E. (1984) Synthesis, properties, and biological activity of some nucleoside cyclic phosphoramidates. *J. Chem. Soc.* Perkin Trans. I, 1471–1474; Juodka, B. A. and Smart, J. (1974) Synthesis of ditribonucleoside a (P→N) amino acid derivatives. Coll. Czech. Chem. Comm. 39, 363–968; Kataoka, S., Imai, J., Yarnaji, N., Kato, M., Saito, M., Kawada, T. and Imai, S. (1989) Alkylacted cAMP derivatives; selective synthesis and biological activities. *Nucleic Acids Res. Sym. Ser.*, 21, 1–2; Kataoka, S., Uchida, R. and Yamaji, N. (1991) A convenient synthesis of adenosine 3',5' cyclic phosphate (cAMP) benzyl and methyl triesters. *Heterocycles* 32, 1351–1356; Kinchington, D., Harvey, J. J., O'Connor, T. J., Jones, B. C. N. M., Devine, K. G., Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3, 107–112; Kodama, K., Morozurni, M., Saitoh, K. I., Kuninaka, H., Yoshino, H. and Saneyoshi, M. (1989) Antitumor activity and pharmacology of 1-β-D-arabinofuranosylcytosine-5'-stearylphosphate; an orally active derivative of 1-β-D-arabinofuranosylcytosine. Jpn. J. Cancer Res. 80, 679–685; Korty, M. and Engels, J. (1979) The effects of adenosine- and guanosine 3',5'-phosphoric and acid benzyl esters on guinea-pig ventricular myocardium. Naunyn-Schmiedeberg's Arch. Pharmacol. 310, 103–111; Kumar, A., Goe, P. L., Jones, A. S. Walker, R. T. Balarini, J. and De Clercq, E. (1990) Synthesis and biological evaluation of some cyclic phosphoramidate nucleoside derivatives. *J. Med. Chem.* 33, 2368–2375; LeBec, C., and Huynh-dinh, T. (1991) Synthesis of lipophilic phosphate triester derivatives of 5-fluorouridine and arabinocytidine as anticancer prodrugs. *Tetrahedron Lett.* 32,6553–6556; Lichtenstein, J., Barner, H. D. and Cohen S. S. (1960) The metabolism of exogenously supplied nucleotides by *Escherichia coli.*, *J. Biol. Chem.* 235, 457–465; Lucthy, J., Von Daeniken, A., Friederich, J. Manthey, B., Zweifel, J., Schlatter, C. and Benn, M. H. (1981) Synthesis and toxicological properties of three naturally occuring cyanoepithioalkanes. Mitt. Geg. Lebensmittelunters. *Hyg.* 72, 131–133 (*Chem. Abstr.* 95, 127093); McGuigan, C. Tollerfield, S. M. and Riley, P. A. (1989) Synthesis and biological evaluation of some phosphate triester derivatives of the anti-viral drug Ara. *Nucleic Acids Res.* 17, 6065–6075; McGuigan, C., Devine, K. G., O'Connor, T. J., Galpin, S. A., Jeffries, D. J. and Kinchington, D. (1990a) Synthesis and evaluation of some novel phosphoramidate derivatives of 3'-azido-3'-deoxythymidine (AZT) as anti-HIV compounds. *Antiviral Chem. Chemother.* 1, 107–113; McGuigan, C., O'Connor, T. J., Nicholls, S. R. Nickson, C. and Kinchington, D. (1990b) Synthesis and anti-HIV activity of some novel substituted dialkyl phosphate derivatives of AZT and ddCyd. *Antiviral Chem. Chemother.* 1, 355–360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. *Antiviral Chem. Chemother.* 1, 25–33; McGuigan, C., Devine, K. G., O'Connor, T. J., and Kinchington, D. (1991) Synthesis and anti-HIV activity of some haloalky phosphoramidate derivatives of 3'-azido-3'deoxythylmidine (AZT); potent activity of the trichloroethyl methoxyalaninyl compound. *Antiviral Res.* 15, 255–263; McGuigan, C., Pathirana, R. N., Mahmood, N., Devine, K. G. and Hay, A. J. (1992) Aryl phosphate derivatives of AZT retain activity against HIV1 in cell lines which are resistant to the action of AZT. *Antiviral Res.* 17, 311–321; McGuigan, C., Pathirana, R. N., Choi, S. M., Kinchington, D. and O'Connor, T. J. (1993a) Phosphoramidate derivatives of AZT as inhibitors of HIV; studies on the caroxyl terminus. *Antiviral Chem. Chemother.* 4,97–101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048–1052.

Alkyl hydrogen phophonate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) Synthesis of purine nucleoside 3',5'-cyclic phosphoramidates. *Tetrahedron Lett.* 269–272; Nagyvary, J. Gohil, R. N., Kirchner, C. R. and Stevens, J. D. (1973) Studies on neutral esters of cyclic AMP, *Biochem. Biophys. Res. Commun.* 55, 1072–1077; Namane, A. Goyette, C., Fillion, M. P., Fillion, G. and Huynh-Dinh, T. (1992) Improved brain delivery of AZT using a glycosyl phosphotriester prodrug. *J. Med. Chem.* 35, 3939–3044; Nargeot, J. Nerbonne, J. M. Engels, J. and Leser, H. A. (1983) Natl. Acad. Sci. U.S.A. 80, 2395–2399; Nelson, K. A., Bentrude, W. G., Stser, W. N. and Hutchinson, J. P. (1987) The question of chair-twist equilibria for the phosphate rings of nucleoside cyclic 3',5'-monophosphates. $^1$HNMR and x-ray crystallographic study of the diasteromers of thymidine phenyl cyclic 3',5'-monophosphate. J. Am. Chem. Soc. 109, 4058–4064; Nerbonne, J. M., Richard, S., Nargeot, J. and Lester, H. A. (1984) New photoactivatable cyclic nucleotides produce intracellular jumps in cyclic AMP and cyclic GMP concentrations. Nature 301, 74–76; Neumann, J. M., Hervè, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. J. Am. Chem. Soc. 111, 4270–4277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodyspastic syndromes with orally administered 1-β-D-rabinofuranosylcytosine-5'-stearylphosphate. Oncology 48, 451–455. Palomino, E., Kessle, D. and Horwitz, J. P. (1989) A dihydropyridine carrier system for sustained delivery of 2',3'dideoxynucleosides to the brain. J. Med. Chem. 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R., Ashton, R., Sutton, D., Harvey, J. J. and Brown, A. G. (1993) Activity of BRL47923 and its oral prodrug, SB203657A against a rauscher murine leukemia virus infection in mice. Antiviral Res. 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesis and evaluation of novel ether lipid nucleoside conjugates for anti-HIV-1 activity. J. Med. Chem. 34, 1408–1414; Pompon, A., Lefebvre, I., Imbach, J. L., Kahn, S. and Farquhar, D. (1994) Decomposition pathways of the mono- and bis (pivaloyloxymethyl) esters of azidothymidine-5'-monophosphate in cell extract and in tissue culture medium; an application of the on-line ISRP-cleaning HPLC technique. Antiviral Chem. Chemother. 5, 91–98; Postemark, T. (1974) Cyclic AMP and cyclic GMP. Anu. Rev. Pharmacol. 14, 23–33; Prisbe, E. J., Martin, J. C. M., McGee, D. P. C., Barker, M. F., Smee, D. F. Duke, A. E., Matthews, T. R. and Verheyden, J. P. J. (1986) Synthesis and antiherpes virus activity of phosphate and phosphonate derivatives of 9-[(1, 3-dihydroxy-2-propoxy)methyl]guanine. J. Med. Chem. 29, 671–675; Pucch, F., Gosselin, G., Lefebvre, I., Pompon, A., Aubertin, A. M. Dirn, A. and Imbach, J. L. (1993) Intracellular delivery of nucleoside monophosphate through a reductase-mediated activation process. Antiviral Res. 22, 155–174; Pugaeva, V. P., Kochkeva, S. I., Mashbits, F. D. and Eizengart, R. S. (1969). Toxicological assessment and health standard ratings for ethylene sulfide in the industrial atmosphere. Gig. Trf. Prof. Zabol. 13, 47–48 (Chem. Abstr. 72, 212); Robins, R. K. (1984) The potential of nucleotide analogs as inhibitors of retroviruses and tumors. Pharm. Res. 11–18; Rosowsky, A., Kim, S. H., Ross and J. Wick, M. M. (1982) Lipophilic 5'-(alkylphosphate) esters of 1-β-D-arabinofuranosylcytosine and its N⁴-acyl and 2.2'-anhydro-3'O-acyl derivatives as potential prodrugs. J. Med. Chem. 25, 171–178; Ross, W. (1961) Increased sensitivity of the walker turnout towards aromatic nitrogen mustards carrying basic side chains following glucose pretreatment. Biochem. Pharm. 8, 235–240; Ryu, E. K., Ross, R. J., Matsushita, T., MacCoss, M., Hong, C. I. and West, C. R. (1982). Phospholipid-nucleoside conjugates 3. Synthesis and preliminary biological evaluation of 1-β-D-arabinofuranosylcytosine 5'diphosphate[−], 2-diacylglycerols. J. Med. Chem. 25, 1322–1329; Saffhill, R. and Hume, W. J. (1986) The degradation of 5-iododeoxyurindine and 5-bromoeoxyuridine by serum from different sources and its consequences for the use of these compounds for incorporation into DNA. Chem. Biol. Interact. 57, 347–355; Saneyoshi, M., Morozumi, M., Kodama, K., Machida, J., Kuninaka, A. and Yoshino, H. (1980) Synthetic nucleosides and nucleotides XVI. Synthesis and biological evaluations of a series of 1-β-D-arabinofuranosylcytosine 5'-alkyl or arylphosphates. Chem. Pharm. Bull. 28, 2915–2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. Mol. Pharmacol. 41, 441–445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukuawa, K. Matsuda, A. and Ueda, T. (1987) A facile one-step synthesis of 5'-phosphatidylnucleosides by an enzymatic two-phase reaction. Tetrahedron Lett. 28, 199–202; Shuto, S., Itoh, H., Ueda, S., Imamura, S., Kukukawa, K., Tsujino, M. Matsuda, A. and Ueda, T. (1988) A facile enzymatic synthesis of 5'-(3-sn-phosphatidyl)nucleosides and their antileukemic activities. Chem. Pharm. Bull. 36, 209–217. One preferred phosphate prodrug group is the S-acyl-2-thioethyl group, also referred to as "SATE."

Figure 2:
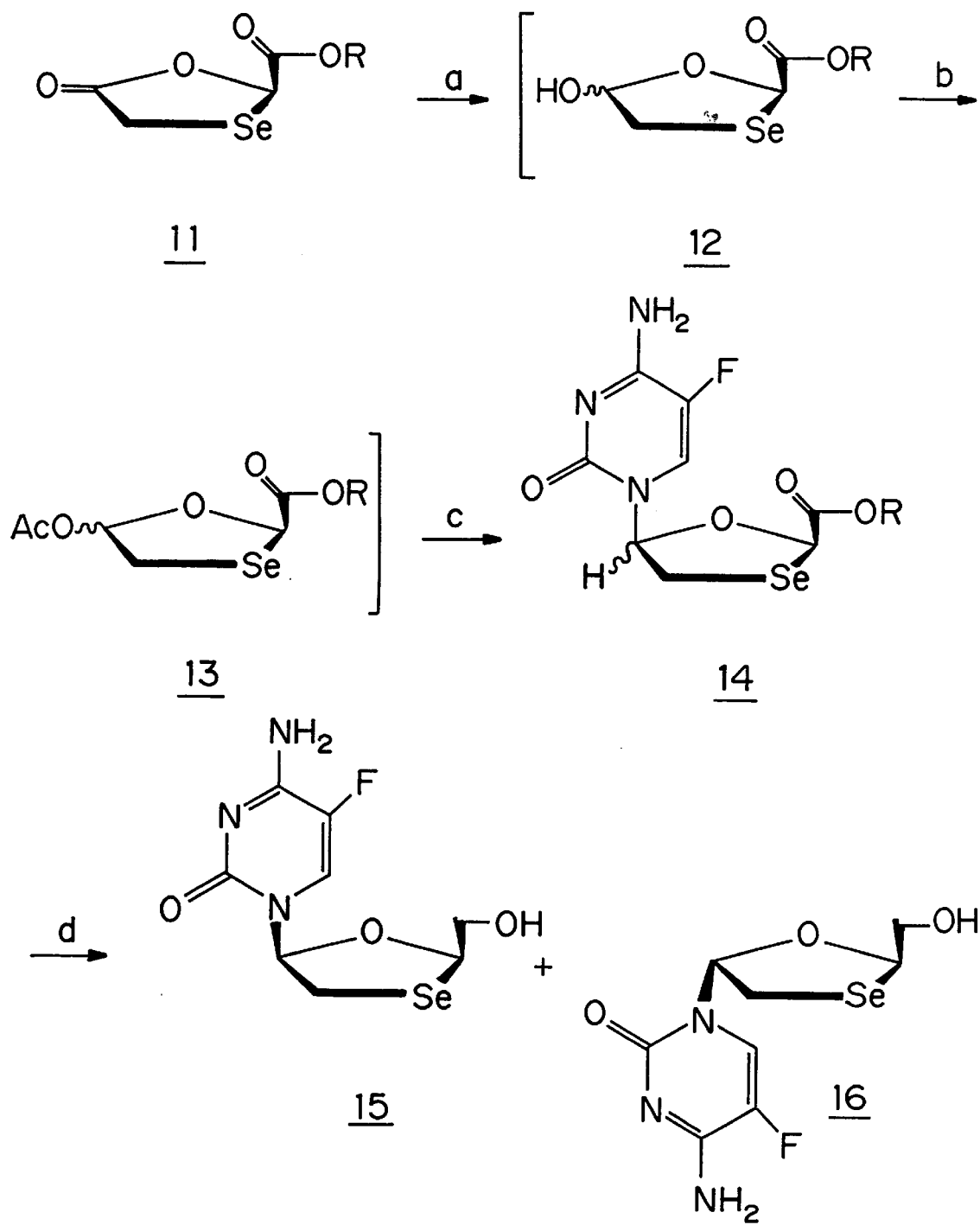
FIG. 2 is an illustration of one process for the preparation of β-D and β-L 1,3-oxaselenolanyl nucleosides according to the present invention, as described in Example 3.
Figure 3:
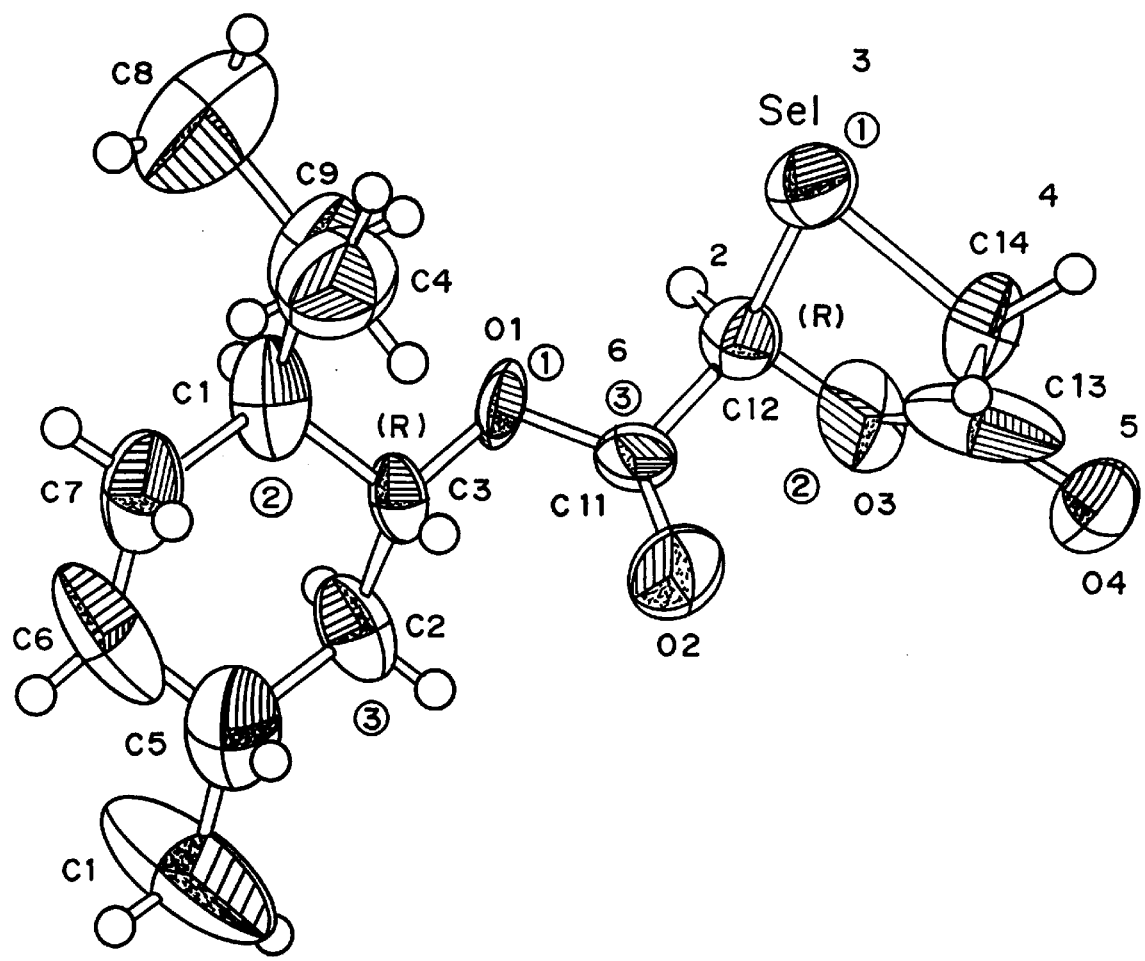
FIG. 3 is the x-ray crystal structure of [2-(1'R,2'S,5'R)-menthyl-(5-one-1,3-oxaselenolane)]-L-carboxylate.
Figure 4:
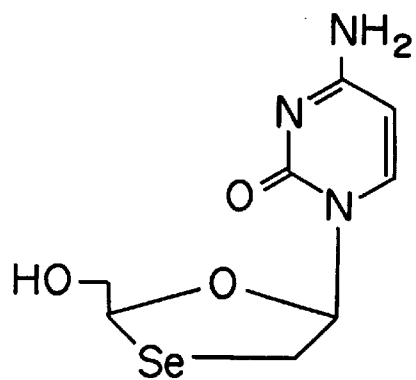
FIG. 4 is an illustration of the structures of the enantiomers of (+)-β-Se-ddC, (−)-β-Se-ddC, (+)-β-Se-FddC and (−)-β-Se-FddC.
Figure 4:
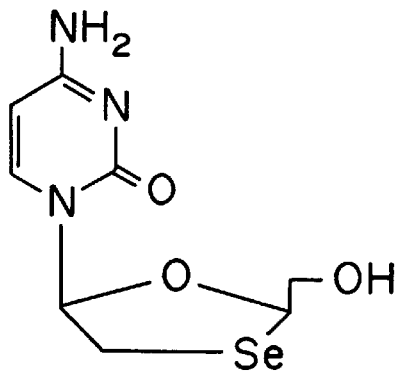
Figure 4:
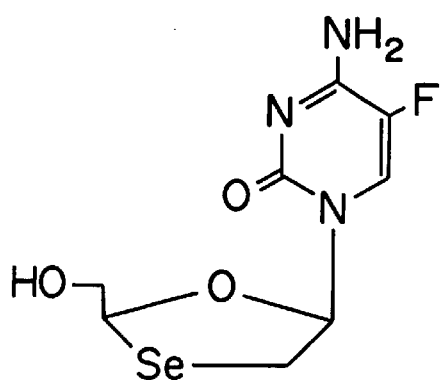
Figure 4:
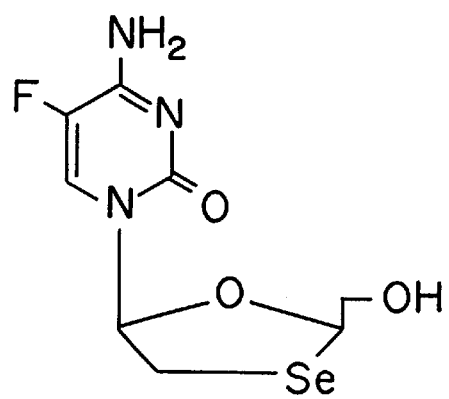

II. Preparation of the Active Compounds 1,3-Oxaselanolanyl nucleosides have evaded production to date because of difficulties encountered with construction of the 1,3-oxaselenolane ring. A process for the production of this ring is now provided herein. One embodiment of the process is illustrated in FIG. 1. Processes are also provided for the preparation of isolated β-D (i.e., 2S,5R) and β-L 1,3-oxaselenolanyl (i.e., 2R,5S) nucleosides. One exemplification of this process is illustrated in FIG. 2. The numbering scheme for the compounds used in the Examples below is provided in FIG. 1.

EXAMPLE 1

Preparation of 1,3-oxaselenolane ring

Selenocyanate was prepared by the method of Kirby in excellent yield. In the first step, ethylbromoacetate ($BrCH_2CO_2Et$) is reacted with potassium selenyl cyanate in alcohol to form selenocyanate 2.

In order to construct lactone 5, it was initially attempted to reduce the selenocyanate 2 with $NaBH_4$ and hydrolyze the resulting ester with aqueous NaOH to the selenol acetic acid, which could be used for the construction of the oxaselenolane ring system 5. However, selenol acetic acid decomposed during the acidification with HCl at pH 2. It has been reported that selenols can be readily oxidized by oxygen in air to stable dimers, which can be reduced back to selenols by $H_3PO_2$. It was discovered that the reduction of the bis(selenoacetic acid) to selenol as well as cyclization can take place in a one-pot reaction without isolation of the intermediates. Thus, dimer 3 was prepared in 81% yield by refluxing 1 with KSeCN in ethanol for 1 hour followed by reduction with NaBH4 at 0° C. for 20–30 minutes. Compared to the recently reported procedure for the preparation of diselenides, this method has the advantages of milder reaction conditions, a high yield and an easier workup. Lactone 5 was then prepared in 33% yield by hydrolysis of 3 with refluxing aqueous acetic acid (50%) for 24 hours followed by the reduction to selenol acetic acid with $H_3PO_2$ which was condensed in situ with 2-benzoyloxyacetaldehyde in the presence of $H_3PO_2$ under nitrogen. For reduction of the lactone 5, it was found that DIBAL-H can selectively reduce the lactone over the ester in THF, while no selectivity was observed in toluene. Thus, sugar acetate 7 was prepared by DIBAL-H reduction of 5 in THF followed by in situ acetylation with acetic anhydride. Condensation of the acetate 7, without purification, with silylated bases in the presence of $SnCl_4$ or TMSOTf gave inseparable mixtures of α- and β-isomers 8a and 8b. Removal of the benzoyl protecting group of 8a and 8b by methylamine or ammonia in methanol yielded the final nucleosides as an α/β-mixture. The α-cytosine nucleoside was obtained by repeated recrystallization of the α/β-mixture from MeOH/Et$_2$O and then methanol, while β-cytosine nucleoside (9a) was obtained by HPLC separation of the mother liquor (C$_{18}$-Column, 20% MeOH in H$_2$O). The β and α-5-fluoro-cytosine nucleosides were obtained by silica gel chromatographic separation of the (α/β-mixture. The structures of the synthesized selenolane nucleosides were confirmed by elemental analyses, $^1$H and $^{13}$C NMR. Stereochemical assignments were determined based on 2D-NOESY experiments in which a correlation between 2'-H and 5'-H of β-isomer 9b was observed while an absence of this correlation in α-isomer 10b was noted. The assignment of stereochemistry was also supported by the upfield chemical shifts of 2'-H in 9a and 9b compared to that of 10a and 10b due to deshielding by the heterocyclic bases.

Stereochemistry

Since the 1' and 4' carbons of the 1,3-oxaselenolanyl moiety of the nucleoside are chiral, their non-hydrogen substituents (the pyrimidine or purine base and the CH$_2$OR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring nucleosides), cis (with both groups "down", which is a nonnaturally occurring configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

The enantiomers of 1,3-oxaselenolanyl nucleoside were obtained in two ways; by chiral chromatography of the nucleoside as described in Example 2 and by fractional crystallization of L-menthol disastereomers of 1,3-oxaselenolane followed by condensation of the resolved 1,3-oxaselenolanyl nucleoside with the desired base in the presence of a Lewis acid that doesn't racemize the oxaselenolane ring.

EXAMPLE 2

Resolution of β-D and β-L enantiomers of 2-hydroxymethyl-4(n-5'-cytosin-1'-yl)-1,3-oxaselenolane and 2-hydroxymethyl-4-(n-5'-fluorocytosin-1'-yl)-1,3-oxaselenolane by chiral chromatography 2-Hydroxymethyl-4-(N-5'-cytosin-1'-yl)-1,3-oxaselenolane and 2-hydroxymethyl-4-(N-5'-fluorocytosin-1'-yl)-1,3-oxaselenolane were resolved by chiral chromatography. The compound (racemic, ca. 2 mg) was dissolved in a minimum amount (ca. 400 μL) of methanol (HPLC grade). The following conditions were used for the resolution: Waters HPLC system; Column: Chiralpak AS 4.6×250 mm; Mobile phase: 2-propanol, Flow rate: 0.80 mL/min; Detector: UV-260 nm; Sparge gas; Helium; Sparge speed: 25 mL/min/solvent reservoir; Injection amount: 20 μL of the solution each time; Retention times; (−)-(2S,5R)-β-L-2',3'-dideoxy-3'-seleno-cytidine, 5.50 min; (+)-(2R,5S)-β-D-2',3'-dideoxy-3'-seleno-cytidine, 6.92 min; (−)-(2S,5R)-β-L-2',3'-dideoxy-5-fluoro-3'-seleno-cytidine, 5.97 min; (+)-(2R,5S)-β-D-2',3'-dideoxy-5-fluoro-3'-seleno-cytidine, 9.62 min. The optical purities of the resolved compounds were >95% ee.

EXAMPLE 3

Resolution of β-D and β-L enantiomers of 1,3-oxaselenolanyl intermediates by conversion to diastereomers followed by separation of diastereomers by fractional crystallization (−)-L-Mentholcarboxya. To a mixture (−)-L-menthol (30 g, 0.2 mol) and gluoxylic acid (36.8 g, 0.4 mol) in toluene (1000 ml) p-TsOH (5 g) was added and the reaction mixture was stiffed at 100 C. for 3 hours. When the reaction finished p-TsOH was neutralized with Et$_3$N and evaporated to dryness. The residue was dissolved in CHCl$_3$ (500 ml), washed with water (3×500 ml), the organic layer was collected, dried (Na$_2$SO$_4$) and evaporated. The oil was crystallized from petroleum either to give (−)-L-mentholcarboxyal as white crystals 20 g (50%): mp 82° C.; $^1$H NMR (CHCl$_3$) δ9.40 (s, 1H, CHO), 4.78 (dt, J=6.45, 11 Hz, 1H, 1-H), 0.75–2.03 (m, 19H); $^{13}$C NMR (CHCl$_3$) δ184.41, 170.22, 87.13, 46.79, 40.40, 34.00, 31.42, 26.11, 23.28, 21.94, 20.68, 16.15. Anal. Calcd for C$_{12}$H$_{20}$O$_3$: C, 67.89; H, 9.50; Found: C, 67.65; H, 9.67. M/S m/e 212.3 (M+).

[2-(1'R,2'S,5'R)-Menthyl-(5-one-1,3-oxaselnolane)]-L-carboxylate (11) and [2-(1'R,2'S,5'R)-Menthyl-(5-one-1,3-oxaselenolane-)]-D-carboxylate To a solution (−)-L-mentholcarboxyal (6.4 g, 30 mmol) in toluene (100 ml) (SeCH$_2$COOH)$_2$ (4.15 g, 15 mmol) was added and reaction mixture was gently heated to 100° C. under argon atmosphere with stirring. Hypophosphorous acid (50% water solution, 2.7 ml) was added dropwise for one hour. The reaction mixture was then refluxed additionally for one hour with vigorous stirring under argon atmosphere. The reaction mixture was evaporated to 20 ml, diluted with EtOAc (250 ml), and washed with water (3×500 ml). The organic layer was collected, dried (Na$_2$SO$_4$) and evaporated. The residue was purified by column chromatography over SiO$_2$ using the mixture EtOAc-Hex (1:10, V/V) as eluent, to give 11 as a solid 3.9 g (77.6%). Crystallization of the mixture compounds from hexanes at room temperature gave 11 as fine colorness needles: mp 106.5° C.; [α]$^{25}_D$=59.86° (c 0.5, CHCl$_3$); $^1$H NMR (CHCl$_3$) δ5.83 (s, 1H, 2'-H), 4.77 (dt, J=4.45, 12 Hz, 1H, 1-H), 3.97 (d, J=15.34 Hz, 1H, 4'-H$_b$), 3.67 (dt, J=15.35 Hz, $^4$J=21.17 Hz, 1H, 4'-H$_a$), 0.75–2.03 (m, 19H); $^{13}$C NMR (CHCl$_3$) δ173.97, 168.67, 76.88, 63.84, 47.07, 40.46, 34.02, 31.38, 26.07, 23.23, 22.65, 21.93, 20.71, 16.11. Anal. Calcd for C$_{14}$H$_{22}$O$_4$Se: C, 50.45; H, 6.65; Found: C, 50.65; H, 6.62. MS m/e 333 (M+). Crystallization mother liquid at −5° C.; [α]$^{25}_D$=−111.71° (c 0.5, CHCl$_3$); $^1$H NMR (CHCl$_3$) δ5.83 (s, 1H, 2'-H), 4.78 (dt, J=4.45, 12 Hz, 1H, 1-H), 3.95 (d, J=15.41 Hz, 1H, 4'-H$_a$), 3.68 (dt, J=15.45 Hz, $^4$J=19.35 Hz, 1H, 4'-H$_a$), 0.75–2.03 (m, 19H); $^{13}$C NMR (CHCl$_3$) δ173.98, 168.63, 76.15, 63.76, 46.95, 39.88, 34.01, 31.32, 26.22, 23.24, 22.98, 21.94, 20.74, 16.14; Anal. Calcd for C$_{14}$H$_{22}$O$_4$Se: C, 50.45; H, 6.65; Found: C, 50.47; H, 6.63. M/S m/e 333 (M+).

1-β-L-(2'-Hydroxymethyl-1,3'-oxaselenolan-5'yl)-5-fluorocytosine (15) and 1-α-L-(2'-hydroxymethyl-1', 3'-oxaselenolane-5'-yl)-5-fluorocytosine (16)

To a solution of lithium tri-tert-butoxyaluminohydride (6 mmol, 6 ml 1M solution in the THF) of the solution lactone 11 (1 g, 3.33 mmol) in the 5 ml TBF was added dropwise at −10° C. for one hour with stirring under argon atmosphere. Then acetic anhydride (2 g, 20 mmol) was added slowly with stirring at −5 −0° C. The reaction mixture was stirred additionally for one hour, diluted with EtOAc (100 ml), washed with water (3×100 ml), dried ($Na_2SO_4$), and concentrated to dryness to give a crude 5'-acetate 13. The sugar acetate 13 was dissolved in $CH_2Cl_2$ (5 ml) and slowly added to silylated 5-flurocytosine prepared by stirring of the mixture 5-fluorocytosine (0.34 g, 2.63 mmol), 2,4,6-collidine (0.8 ml, 6.61 mmol) and, tert-butyldimethylsilyl trifuloromethanesulfonate (1.32 g, 5.08 mmol) for one hour under argon atmosphere. To the resulting mixture was added iodotrimethylsilane (0.35 g, 1.75 mmol), stirred at room temperature for 18 hours, diluted with $CHCl_3$ (100 ml), poured into aq. $Na_2S_2O_3$ (100 ml), washed with water, dried ($Na_2SO_4$), and concentrated to dryness. The residue was purified by flash-chromatography over silica gel using $CHCl_3$ as eluent to give crude 13 as solid (0.15 g, 11.2%). $^1$H NMR ($CDCl_3$) δ8.35 (d, J=6.3 Hz, 1H, 6-H), 7.55, 7.53 (2×br s, 2H, $NH_2$), 6.45 (m, 1-h, 5'-H), 6.14 (m, 1H, 2'-H), 4.79 (m, 1H, 1-H), 3.66 (m, 2H, 6'-$H_{ab}$). A solution of the compound 14 (0.15 g, 0.33 mmol) in THF (10 ml) at room temperature for one hour. The reaction mixture was stirred additionally 1 hour, quenched with MeOH (5 ml) and resulting mixture was applied to short column with silica gel. The column was eluted with mixture EtOAc-Hex-MeOH (1:1:1, V/V, 100 ml). The eluent was concentrated to dryness and resulting solid purified over $SiO_2$ using $CHCl_3$-EtOH (20:1, V/V) as eluent to give mixture β-L- (15) and α-L-nucleosides (16) like white solid 0.033 g (34%). The mixture was reseparated by column over $SiO_2$ using as eluent mixture four solvents EtOAc-Hex-$CHCl_3$-EtOH (5:5:2:1, V/V).

1-β-L-(2'-Hydroxymethyl-1',3'-oxaselenolane-5'-yl)-5-fluorocytosine (15)

White solid (0.01 g, 10.2%); mp 186–189° C. (MeOh); $[α]^{25}_D$=−55° (c 0.35, MEOH); UV ($H_2$)) $λ_{max}$ 280.0 nm (ε 10646, pH2), 280.0 nm (ε 7764, pH 11); $^1$H NMR (DMSO-$d_6$) δ8.07 (d, J=7.1 Hz, 1H, 6-H), 7.92, 7.67 (2×br s, 2H, $NH_2$, $D_2O$ exchangeable), 6.06 (t, J=2.96 Hz, 1-H, 5'-H), 5.42 (t, J=4.82 Hz, 1H, 2'-H), 5.34 (t, J=5.68 Hz, 1H, OH, $D_2O$ exchangeable), 3.81 (m, 1H, 6'-$H_a$), 3.68 (m, 1H, 6'-$H_b$), 3.39 (dd, J=4.84 Hz, 1H, 4'-$H_b$), 3.08 (dd, J=8.11 Hz, 1H, 4'-$H_a$); $^{13}$C NMR (DMSO-$d_6$) δ157.7 (C=O), 153.3 (4-C), 137.6 (6-C), 135.2 (5-C), 88.3 (5'-C), 78.2 (2'-C), 64.0 (6'-C), 28.9 (4'-C); Anal. Calcd for $C_8H_{10}O_3N_3FSe$: C, 32.67; H, 3.43; N, 14.29; Found: C, 32.62; H, 3.51; N, 14.41. M/S m/e 295 (M+).

1-α-L-(2'-Hydroxymethyl-1',3'-oxaselenolane-5'-yl)-5-flurocytosine (16)

White solid (0.013 g, 13.2%); mp 193–195° C. (MeOH); $[α]^{25}_D$=+84.20° (c 0.26,MeOH); UV ($H_2O$) $λ_{max}$ 279.5 nm (ε 7638, pH 7), 287.5 nm (ε 9015, pH 2), 281.0 nm (ε 6929, pH 11); $^1$H NMR (DMSO-$d_6$) δ7.91 (d, J=7.1 Hz, 1H, 6-H), 7.88, 7.63 (2×br s, 2H, $NH_2$, $D_2O$ exchangeable), 6.35 (t, J=4.95 Hz, 1-H, 5'-H), 5.63 (dd, J=4.83 Hz, 1H, 2'-H), 5.28 (t, J=5.67 Hz, 1H, OH, $D_2O$ exchangeable), 3.70 (m, 1H, 6'-$H_a$), 3.53 (m, IH, 6'-Hb), 3.47 (dd, J=4.82 Hz, 1H, 4'-$H_a$), 3.24 (dd, J=7.88 Hz, 1H, 4'-$H_b$); $^{13}$C NMR (DMSO-$d_6$) δ157.8 (C=O), 153.2 (4-C), 137.3 (6-C), 134.9 (5-C), 88.6 (5'-C), 80.9 (2'-c), 65.5 (6'-C), 29.4 (4'-C); Anal. Calcd for $C_8H_{10}O_3N_3FSe$: C, 32.67; H, 3.43; N, 14.29; Found: C, 32.59; H, 3.49; N, 14.20. M/S m/e 295 (M+). Synthesis of nucleosides 8 and 9 has been accomplished in same manner from a lactone 3 (1 g, 3.33 mmol) to give 1-β-D-(2'-hydroxymethyl-1',3'-oxaselenolane-5'-yl)-5-fluorocytosine 8. White solid (0.007 g, 8.5%); mp 186–189° C. (MeOH); $[α]^{25}_D$=+56.21°(c 0.33, MeOH); UV ($H_2O$) $λ_{max}$ 280.0 nm (ε 8576, pH 7), 289.0 nm (ε 10456, pH 2), 280.0 nm (ε 7795, pH 11): 1H NMR (DMSO-$d_6$) δ8.07 (d, J=7.1 Hz, 1H, 6-H), 7.92, 7.67 (2×br s, 2H, $NH_2$, $D_2O$ exchangeable), 6.06 (5, J=2.96 Hz, 1-H, 5'-H), 5.42 (5, J=4.82 Hz, 1-H, 2'-H), 5.34 (5, J=5.68 Hz, 1H, OH, $D_2O$ exchangeable), 3.81 (m, 1H, 6'-$H_a$), 3.68 (m, 1H, 6'-$H_b$), 3.39 (dd, J=4.84 Hz, 1H, 4'-$H_b$), 3.08 (dd, J=8.11 Hz, 1H, 4'-$H_a$); $^{13}$C NMR (DMSO-$d_6$ (δ157.7 (C=O), 153.3 (4-C), 137.6 (6-C), 135.2 (5-C), 88.3 (5'-C), 78.2 (2'-C), 64.0 (6'-C), 28.9 (4'-C); Anal. Calcd for $C_8H_{10}O_3N_3FSe$: C, 32.67; H, 3.43; N, 14.29; Found: C, 32.57; H, 3.39; N, 14.35. M/S m/e 295 (M+).

1-α-D-(2'-Hydroxymethy-1',3'-oxaselenolan-5'-yl)-5-fluorocytosine 9

White solid (0.01 g, 10%); mp 193–195° C. (MeOH); $[α]^{25}_D$=−85.49° (c 0.31, MeOH); UV ($H_2O$) $λ_{max}$ 279.5 nm (ε 7644, pH 7), 287.5 nm (ε 9067, pH 2), 281.0 nm (ε 6983, Ph 11); $^1$H NMR (DMSO-$d_6$) δ7.91 (d, J=7.1 Hz, 1H, 6-H), 7.88, 7.63 (2×br s, SH, $NH_2$, $D_2O$ exchangeable), 6.35 (5, J=4.95 Hz, 1-H, 5'-H), 5.63 (dd, J=4.83 Hz, 1H, 2'-H), 5.28 (5, J=5.67 Hz, 1H, OH, $D_2O$ exchangeable), 3.70 (m, IH, 6'-$H_a$); $^{13}$C NMR (DMSO-$d_6$) δ157.8 (C=O), 153.2 (4-C), 137.3 (6-C), 134.9 (5-C), 88.6 (5'-C), 80.9 (2'-C), 65.5 (6'-C), 29.4 (4'-C); Anal. Calcd for $C_8H_{10}O_3N_3FSe$: C, 32.67; H, 3.43; N, 14,29; Found: C, 32.67; H, 3.48; N, 14.47. M/S m/e 295 (M+).

Table 1 provides the separation results for (+)-β-Se-FddC, (−)-β-Se-FddC, (+)-α-Se-FddC, (−)-α-Se-FddC and (−)-β-Se-ddC and compares the retention times and absorption wavelengths of these compounds with (−)-β-FTC and (+)-β-FTC.

TABLE 1

| | Separation results | | | |
|---|---|---|---|---|
| Compounds | Retention time (min) | Absorption wavelength, nm | Optical rotation (degrees) | Purity |
| (−)-β-Se-FddC | 4.8 | 247.3, 285.1 | −103.2 (c0.5, MeOH) | 100 |
| (+)-β-Se-FddC | 7.7 | 247.3, 285.1 | +96.8 (c).5, MeOH) | 100 |
| (+)-α-Se-FddC | 4.8 | 247.3, 285.1 | ND | 100 |
| (+α-Se-FddC | 6.6 | 247.3, 285.1 | ND | 90 |
| (−)-β-FTC | 4.7 | 242.6, 285.1 | — | — |
| (+)-β-FTC | 6.9 | 242.6, 285.1 | — | — |
| (−)-β-Se-ddC | 9.5 | 242.6, 270.9 | −72.4 (c1, DMSO) | 100 |
| (+)-β-Se-ddC | 11.9 | 242.6, 270.9 | +56.4 (c1, DMSO) | 96 |
| (−)-α-Se-ddC | ND | 242.6, 270.9 | 46.7 (c1, DMSO) | 100 |
| (+)-α-Se-ddC | ND | 242.6, 270.9 | +26.1 (c1, DMSO) | 94 |

Table 2 provides resolution and separation factors of compounds separated on ChiralPak AS. The separation factor is defined as the retention time of the second eluted isomer minus dead time per the difference between retention time of the first eleuted isomer and dead time. The resolution factor is defined as twice the difference of retention time of (+) and (−) isomers per the band width of the two peaks.

TABLE 2

Comparison of separations on ChiralPak AS.
Chromatagraphic conditions: mobil phase; 2-propanol;
100 μg in 10 μl of methanol were injected;
UV detection at 254 nm; Flow rate at ml/min.

| Compounds | Separation factor α[a] | Resolution $R_2$[b] |
|---|---|---|
| racemic α-Se-FddC | 2.34 | 1.91 |
| racemic β-Se-FddC | 3.14 | 3.28 |
| racemic β-FTC | 2.84 | 2.87 |

[a]Separation factor = (retention time of the second eluted isomer − dead time)/(retention time of the first eluted isomer − dead time).
[b]Resolution factor = 2 × [difference of retention time of (+) and (−) isomers]/(the band width of the two peaks).

Table 3 gives the effects of various solvent rations and flow rate chiral paration of racemic β-Se-ddC.

TABLE 3

The effects of various solvent ratios and flow rate chiral paration of racemic β-Se-ddC

| EtOH:Hexane Ratio | Flow-rate (ml/min) | Resolution $R_2$ | First eluted peak area (uV*sec × $10^7$) | First peak retention time (min) |
|---|---|---|---|---|
| 100:0 | 0.8 | 1.25 | 1.25 | 4.65 |
| 50:50 | 0.8 | 1.48 | 1.13 | 6.06 |
| 40:60 | 0.8 | 1.76 | 1.11 | 7.21 |
| 30:70 | 0.8 | 2.05 | 1.08 | 9.71 |
| 30:70 | 1.0 | 1.98 | 0.88 | 7.83 |
| 30:70 | 1.4 | 1.90 | 0.64 | 5.59 |
| 20:80 | 1.4 | 2.12 | 0.61 | 9.78 |
| 40:60 | 0.6 | 1.75 | 1.46 | 9.53 |

Mono, di, and triphosphate derivatives of the active nucleosides can be prepared as described according to published methods. The monophosphate can be prepared according to the procedure of Imai, et al., *J. Org. Chem.*, 34(6), 1547–1550 (June 1969). The diphosphate can be prepared according to the procedure of Davisson, et al., *J. Org. Chem.*, 52(9), 1794–1801 (1987). The triphosphate can be prepared according to the procedure of Hoard, et al., *J. Am. Chem. Soc.*, 87(8), 1785–1788 (1965).

III. Combination and Alternation Therapies

It has been recognized that drug-resistant variants of HIV and HBV can emerge after prolonged treatment with an antiviral agent. Drug resistance most typically occurs by mutation of a gene that encodes for an enzyme used in the viral lifecycle, and most typically in the case of HIV, reverse transcriptase, protease, or DNA polymerase, and in the case of HBV, DNA polymerase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor, In other embodiments, the second (or third) compound can be a pyrophosphate analog, or a fusion binding inhibitor. A list compiling resistance data of in vitro and in vivo for a number of antiviral compounds is found in Schinazi, et al., "Mutations in retroviral genes associated with drug resistance," *International Antiviral News,* Volume 1(4), International Medical Press 1996.

Preferred compounds for combination or alternation therapy for the treatment of HBV include FTC (the (−)-enantiomer or the racemate), L-FMAU, interferon, β-D-dioxoxlanyl-guanine (DXG), β-D-dioxolanyl-2,6-diaminopurine (DAPD), and β-D-dioxolanyl-6-chloropurine (ACP), famciclovir, penciclovir, BMS-200475, bis bom PMEA (adefovir, dipivoxil); lobucavir, ganciclovir, and ribavarin.

Preferred examples of antiviral agents that can be used in combination or alternation with the compounds disclosed herein for HWV therapy include 2-hydroxymethyl-5-(5-fluorocytosin-1-yl)-1,3-oxathiolane (FTC); the (−)-enantiomer of 2-hydroxymethyl-5-(cyostin-1-yl)-1,3-oxathiolane (3TC); carbovir, acyclovir, interferon, AZT, DDI, DDC, D4T, CS-92 (3'-azido-2',3-dideoxy-5-methyl-cytidine), and β-D-dioxolane nucleosides such as β-D-dioxolanyl-guanine (DXG), β-D-dioxolanyl-4chloropurine (ACP), and MKC-442 (6-benzyl-1-(ethoxymethyl)-5-isopropyl uracil.

Preferred protease inhibitors include crixovan (Merck), nelfinavir (Agouron), ritonavir (Abbot), saquinavir (Roche), and DMP450 (DuPont Merck).

Nonlimiting examples of compounds that can be administered in combination or alternation with any of the 1,3-oxaselenolenyl nucleosides include (1S,4R)-4-[2-amino-6-cyclopropyl-amino)-9H-purin-9-yl]-2-cyclopentene-1-methanol succinate ("1592", a carbovir analog; Glaxo Wellcome); 3TC: (−)-β-L-2',3'-dideoxy-3'-thiacytidine (Glaxo Wellcome); a-APA R 18893: a-nitro-anilino-phenylacetamide; A-77003; C2 symmetry-based protease inhibitor (Abbott); A-75925: C2 symmetry-based protease inhibitor (Abbott); AAP-BHAP: bisheteroarylpiperazine analog (Upjohn); ABT-538: C2 symmetry-based protease inhibitor (Abbott); AzddU: 3'-azido-2',3'-dideoxyuridine; AZT: 3'-azido-3'-deoxythymidine (Glaxo Wellcome); AZT-p-ddI: 3'-azido-3'-deoxythymidilyl-(5',5')-2',3'-dideoxyinosinic acid (Ivax): BHAP: bisheteroarylpiperazine; BILA 1906: N-{1S-{{{3-[2S-{(1,1-dimethylethyl) amino]carbonyl}-4R-]3-pyridinylmethyl)thio]-1-piperidinyl]-2R-hydroxy-1S-(phenylmethyl)-propyl]amino] carbonyl]-2-methylpropyl}-2-quinolinecarboxamride (Bio Mega/Boehringer-Ingelheim); BILA 2185: N-(1,1-dimethyllethyl)-1-[2S-[[2-2,6-dimethyphenoxy)-1-oxoethyl]amnino]2-R-hydroxy-4-phenylbutyl]4R-pyridinylthio-2-piperidinecarboxamide (Bio Mega/Boehringer-Ingelheim); BM+51.0836: thiazolo-isoindolinone derivative; BMS 186,318: aminodiol derivative HIV-1 protease inhibitor (Bristo-Myers-Squibb); d4API: 9-[2,5-dihydro-5-(phosphonomethoxy)-2-furane] adenine (Gilead); d4C: 2',3'-didehydro-2',3'-dideoxycytidine; d4T: 2',3'-didehydro-3'-deoxythymidine (Bristol-Myers-Squibb); ddC; 2',3'-dideoxycytidine (Roche); ddI: 2',3'-dideoxyinosine (Bristol-Myers-Squibb); DMP-266: 1 1,4-dihydro-2H-3,1-benzoxazin-2-one; DMP450: {[4R-(4-a,5-a,6-b,7-b)]-hexahydro-5,6-bis (hydroxy)-1,3-bis(3-amino)phenyl]methyl)-4,7-bis (phenylmethyl)-2H-1,3-diazpin-2-one}-bismesylate (Avid); DXG:(−)-β-D-dioxolane-guanosine (Triangle); EBU-dM:5-ethyl-1-ethoxymethyl-6(3,5-dimethylbenzyl)uracil; E-EBU: 5-ethyl-1-ethoxymethyl-6-benzyluracil; DS: dextran sulfate;

E-EPSeU: 1-(ethoxymethyl)-(6-phenylselenyl)-5-ethyluracil; E-EPU: 1-(ethoxymethyl)-(6-phenyl-thio)-5-ethyluracil; FTC: β-2',3'-dideoxy-5-fluoro-3'-thiacytidine (Triangle); HBY097: S-4-isopropoxycarbonyl-6-methoxy-3-(methylthio-methyl)-3,4-dihydroquinoxalin-2(1H)-thione; HEPT: 1-[2-hydroxyethoxy)methyl]6-(phenylthio)thymine; HIV-1:human immunodeficiency virus type 1; JM2763: 1,1'-(1,3-propanediyl)bis-1,4,8,11-tetraazacyclotetradecane (Johnson Matthey); JM3100:1,1-[1,4-phenylenebis-(methylene)]-bis-1,4,8,11-tetraazacyclotetradecane (Johnson Matthey); KNI-272: (2S,3S)-3-amino-2-hydroxy-4-phenylbutyric acid-containing tripeptide; L-697,593; 5-ethyl-6-methyl-3-(2-phthalimido-ethyl)pyridin-2(1H)-one; L-735,524: hydroxy-aminopentane amide HIV-1 protease inhibitor (Merck); L697,661: 3-{[(-4,7-dichloro-1,3-benzoxazol-2-yl)methyl]amino}-5-ethyl-6-methylpyridin-2(1H)-one; L-FDDC: (0)-β-L-5-fluoro-2',3'-dideoxycytidine; L-FDOC:(–)-β-L-5-fluoro-dioxolane cytosine; MKC-442: 6-benzyl-1-ethoxymethyl-5-isopropyluracil (I-EBU: Triangle/Mitsubishi); Nevirapine: 11-cyclopropyl-5,11-dihydro-4-methyl-6H-dipyridol[3,2-b:2',3'-e]diazepin-6-one (Boehringer-Ingelheim); NSC648400: 1-benzyloxymethyl-5-ethyl(alpha-pyridylthio)uracil (E-BPTU); P9941: [2-pyridylacetyl-IlePheAla-y(CHOH)]2 (Dupont Merck); PFA: phosphonoformate (foscarnet; Astra); PMEA: 9-(2-phosphonylmethoxyethyl)adenine (Gilead); PMPA: (R)-9-(2-phosphonylmethoxypropyl)adenine (Gilead); Ro 31-8959: hydroxyethylamine derivative HIV-1 protease inhibitor (Roche); RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydroquinoxalin-2(1H) thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1-jk][1,4]-benzodiazepin-2(1H)-thione (Janssen); TIBO 82913: (+)-(5S)-4,5,6,7,-tetrahydrdo-9-chloro-5-methyl-6-(3-methyl-2-butenyl)imidazo-[4,5,1jk]-[1,4]benzodiazepin-2(1H)-thione (Janssen); TSAO-m3T:[2',5'-bis-O-(tert-butyldimethylsilyl)-3'-spiro-5'-(4'-amino-1',2'-oxathiole-2',2'-dioxide)]-b-D-pentofuranosyl-N3-methylthymine; U90152: 1-[3-[1-methylethyl)-amino]-2-pyridinyl]-4-[[5-[(methylsulphonyl)-amino]-1H-indol-2yl]carbonyl] piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethyl-sulphonamide protease inhibitor (Vertex); VS478:hydroxyethylsulphonamide protease inhibitor (vertex); XM 323: cyclic urea protease inhibitor (Dupont Merck).

IV. Ability of 1,3-oxaselenolanyl Nucleosides to Inhibit the Replication of HIV and HBV The ability of nucleosides to inhibit HIV can be measured by various experimental techniques. The technique used herein, and described in detail below, measures the inhibition of viral replication in phytohemaggluinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is proportional to the amount of virus produced.

EXAMPLE 4

Anti-HIV Activity of 1,3-Oxaselenolanyl Nucleosides

2-Hydroxymethyl-4-(N-5'-cytosin-1'-yl)-1,3-oxaselenolane and 2-hydroxymethyl-4-(N-5'-fluorocytosin-1'-yl)-1,3-oxaselenolane were tested for anti-HIV activity.

Three-day old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infections dose (TICD 50) per ml and cultured in the presence and absence of various concentrations of antiviral compounds.

Approximately one hour after infection, the medium, with the compound to be tested (2 times the final concentration in medium) or without compound, was added to the flasks (5 ml; final volume 10 ml). AZT was used as a positive control.

The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal, et al. (*J. Immun. Meth.* 76, 171–183, 1985) and Spira, et al. (*J. Clin. Meth.* 25, 97–99, 1987), except that fungizone was not included in the medium (see Schinazi, et al.,*Antimicrob. Agents Chemother.* 32, 1784–1787 (1988); Id., 34:1061–1067 (1990)).

On day 6, the cells and supernatant were tnansferred to a 15 ml tube and centrifuged at about 900 g for 10 minutes. Five ml of supernatant was removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant. Virus from smaller volumes of supernatant (1 ml) can also be concentrated by centriguation prior to solubilization and determination of reverse transcriptase levels.

The median effective ($EC_{50}$) concentration was determined by the median effect-method (*Antimicrob. Agents Chemother.* 30, 491–498 (1986)). Briefly, the percent inhibition of virus, as determined from measurements of reverse transcriptase, is plotted versus the micromolar concentration of compound. The $EC_{50}$ is the concentration of compound at which there is a 50% inhibition of viral growth.

Mitogen stimulated uninfected human PBM cells ($3.8 \times 10^5$ cells/ml) were cultured in the presence and absence of drug under similar conditions as those used for the antiviral assay described above. The cells were counted after 6 days using a hemacytometer and the trypan blue exclusion method, as described by Schinazi, et al., (*Antimicrobial Agents and Chemotherapy*, 22(3), 499 (1982)). The $IC_{50}$ is the concentration of compound which inhibits 50% of normal cell growth.

Table 4 provides the $EC_{50}$ values (concentration of nucleoside that inhibits the replication of the virus by 50% in PBM cells, estimated 10% error factor) and $IC_{50}$ values (concentration of nucleoside that inhibits 50% of the growth of mitogen-stimulated uninfected human PBM cells, CEM cells, and in Vero cells) of 2-hydroxymethyl-4-(N-5'-cytosin-1'-yl)-1,3-oxaselenolane and 2-hydroxymethyl-4-(N-5'-fluorocytosin-1'-yl)-1,3-oxaselenolane.

TABLE 4

Anti-HIV activities of oxaselenolane nucleosides

| Base | Anti-HIV Activity in PBM Cells ($EC_{50}$ μM) | Toxicity ($IC_{50}$ μM) PMB CEM Vero |
|---|---|---|
| Cytosine | 0.88 | >100 >100 >100 |
| 5-F-Cytosine | 0.07 | >100 >100 >100 |

Table 5 provides the percent purity, $EC_{50}$ values (μM), $EC_{90}$ values (μM) and $IC_{50}$ values in PBM cell of racemic β-Se-ddC, its (+)- and (−)-isomers and for racemic β-Se-FddC, its (+)- and (−)-isomers.

TABLE 5

Anti-HIV Activity and Cytotoxicity of Racemates and Enantiomers of Oxaselenolane Cytosine Nucleosides

| Compound | Enantiomer | % Purity | $EC_{50}$ μM | $EC_{90}$ μM | $IC_{50}$ PBM |
|---|---|---|---|---|---|
| β-Se-ddC | ± | 50 | 2.69 | 209 | >100 |
| β-Se-ddC | − | ≈100 | 0.88 | 5.42 | >100 |
| β-Se-ddC | + | ≈96 | 3.39 | 677 | >100 |
| β-Se-FddC | ± | 50 | 5.55 | 16.41 | >100 |
| β-Se-FddC | − | ≈100 | 0.21 | 1.05 | >100 |
| β-Se-FddC | + | ≈100 | 41.9 | 164 | >100 |

The anti-HIV activity of β-Se-ddC, its (+)- and (−)-isomers and racemic β-Se-FddC, its (+)- and (−)-isomers were also tested in PBM cells infected with HIV that exhibits a mutation at codon 184 in the reverse transcriptase gene. The results are provided in Table 6. As indicated, racemic and (−)-β-Se-ddC exhibits significant activity against the mutated virus.

TABLE 6

Effect of Oxaselenolane Cytosine Nucleosides Against Cloned M184 HIV-1

| Compound | Enantiomer | % Purity | Virus | $EC_{50}$ μM | $EC_{90}$ μM | FI $EC_{50}$ | FI $EC_{90}$ |
|---|---|---|---|---|---|---|---|
| β-Se-ddC | ± | 50 | xxBRU | 1.84 | 6.90 | — | — |
| β-Se-ddC | − | ≈100 | xxBRU | 0.11 | 0.95 | — | — |
| β-Se-ddC | + | ≈96 | xxBRU | 8.62 | 35.1 | — | — |
| β-Se-FddC | ± | 50 | M184V | 108 | 337 | 59 | 49 |
| β-Se-FddC | − | ≈100 | M184V | >50 | >50 | >455 | >53 |
| β-Se-FddC | + | ≈96 | M184V | >50 | >50 | >6 | >1 |

Note:
FI (fold increase) $EC_{50}$ = $EC_{50}$ data from cloned virus/$EC_{50}$ date from xxBRU

EXAMPLE 5

Anti-HBV Activity of 1,3-Oxaselenolanyl Nucleosides

The ability of the active compounds to inhibit the growth of virus in 2.2.15 cell cultures (HepG2 cells transformed with hepatitis virion) can be evaluated as described in detail below.

A summary and description of the assay for antiviral effects in this culture system and the analysis of HBV DNA has been described (Korba and Milman, 1991, *Antiviral Res.*, 15:217). The antiviral evaluations are performed on two separate passages of cells. All wells, in all plates, are seeded at the same density and at the same time.

Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are considered to be statistically significant (P<0.05). The levels of integrated HBV DNA in each cellular DNA preparation (which remain constant on a per cell basis in these experiments) are used to calculate the levels of intracellular HBV DNA forms, thereby ensuring that equal amounts of cellular DNA are compared between separate samples.

Typical values for extracellular HBV virion DNA in untreated cells range rom 50 to 150 pg/ml culture medium (average of approximately 76 pg/ml). Intracellular HBV DNA replication intermediates in untreated cells range from 50 to 100 μg/pg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and milman, 1991, *Antiviral Res.*, 15:217).

The manner in which the hybridization analyses are performed for these experiments results in an equivalence of approximately 1.0 pg of intracellular HBV DNA to 2–3 genomic copies per cell and 1.0 pg/ml of extracellular HBV DNA to $3 \times 10^5$ viral particles/ml.

Toxicity analyses can be performed to assess whether any observed antiviral effects are due to a general effect on cell viability. One method that can be used is the measurement of the uptake of neutral red dye, a standard and widely used assay for cell viability in a variety of virus-host systems, including HSV and HIV. Toxicity analyses are performed in 96-well flat bottomed tissue culture plates. Cells for the toxicity analyses are cultured and treated with test compounds with the same schedule as described for the antiviral evaluations below. Each compound is tested at 4 concentrations, each in triplicate cultures (wells "A", "B", and "C"). Uptake of neutral red dye is used to determine the relative level of toxicity. The absorbance of internalized dye at 510 nm ($A_{sin}$) is used for the quantitative analysis. Values are presented as a percentage of the average $A_{sin}$ values in 9 separate cultures of untreated cells maintained on the same 96-well plate as the test compounds.

EXAMPLE 6

Use of 1,3-Oxaselenolanyl Nucleosides to Treat Abnormal Cellular Proliferation Some of the 1,3-oxaselenolanyl nucleosides described herein can be used to treat abnormal cellular proliferation, including tumors and cancer. The extent of antiproliferative activity can be easily assessed by assaying the compound according to the procedure below in a CEM cell or other tumor or proliferative cell line assay. CEM cells are human lymphoma cells (a T-lymphoblastoid cell line that can be obtained from ATCC, Rockville, Md.). The toxicity of a compound to CEM cells provides useful information regarding the activity of the compound against tumors. The toxicity is measured as $IC_{50}$ micromolar). The $IC_{50}$ refers to that concentration of test compound that inhibits the growth of 50% of the tumor cells in the culture. The lower the $IC_{50}$, the more active the compound is as an antitumor agent. In general, a 1,3-oxaselenolanyl nucleoside exhibits antitumor activity and can be used in the treatment of abnormal proliferation of cells if it exhibits a toxicity in CEM or other immortalized tumor cell line of less than 10 micromolar, more preferably, less than approximately 5 micromolar, and most preferably, less than 1 micromolar.

Drug solutions, including cycloheximide as a positive control, are plated in triplicate in 50 μl growth medium at 2 times the final concentration and allowed to equilibrate at 37° C. in a 5% $CO_2$ incubator. Log phase cells are added in 50 μl growth medium to a final concentration of $2.5 \times 10^3$ (CEM and SK-MEL-28), $5 \times 10^3$ (MNAN, MDA-MB435s, SKMES-1, DU-145, Lncap), or $1 \times 10^4$ (PC-3, MCF-7) cells/well and incubated for 3 (DU-145, PC-3, MNAN), 4 (MCF-7, SK-MEL-28, CEM), or 5 (SK-MES-1, MDA-MBA435s, LNCaP) days at 37° C. under a 5% $CO_2$ air atmosphere. Control wells include media alone (blank) and cells plus media without drug. After growth period, 15 μl of Cell Titer 96 kit assay dye solution (Promega, Madison, Wis.) are added to each well and the plates are incubated 8 hr at 37° C. in a 5% $CO_2$ incubator. Promega Cell Titer 96 kit assay stop solution is added to each well and incubated 4–8 hr in the incubator. Absorbance is read at 570 nm, blanking on the medium-only wells using a Biotek Biokinetics plate read (Biotek, Winooski, Vt.). Average percent inhibition of growth compared to the untreated control is calculated. $IC_{50}$, $IC_{90}$, slope and r value are calculated by the method of Chou and Talaly. Chou T-C, Talalay P. Quantitative analysis of dose-effect relationships: The combined effects of multiple drugs or enzyme inhibitors. *Adv Enzyme Regul.* 1984;22:27–55.

IV. Preparation of Pharmaceutical Compositions

Humans suffering from diseases caused by any of the diseases described herein, including HIV infection, HBV infection, or abnormal cellular proliferation, can be treated by administering to the patient an effective amount of a 1,3-oxaselenolanyl nucleoside optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, especially HIV and HBV replication, without causing serious toxic effects in the patient treated. By "inhibitory amount," it is meant an amount of active ingredient sufficient to exert an inhibitory effect as measured by, for example, an assay such as the ones described herein.

A preferred dose of the compound for all the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art The compound is conveniently administered in unit or any suitable dosage form, including but not limited to one containing 7 to 3000 mg, preferably 70 to 1400 mg of active ingredient per unit dosage form. An oral dosage of 50–1000 mg is usually convenient.

Ideally the active ingredient should be administered to achieve peak plasma concentrations of the active compound of from about 0.2 to 70 pM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salt thereof can also be mixed with other active materials that do not impair the desired action, or with materials that supplement the desired action, such as antibiotics, antifungals, antiinflammatories, protease inhibitors, or other nucleoside or nonnucleoside antiviral agents, as discussed in more detail above. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) such as stearoyl phosphatidyl ethanolamine, stearoyl phosphatidyl choline, arachadoyl phosphatidyl choline and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A 1,3-oxaselenolane lactone of the formula:

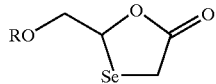

wherein R is hydrogen, acyl, a mono-, di- or triphosphate ester, or an ether lipid, or a pharmaceutically acceptable salt thereof.

2. A process for preparing a 1,3-oxaselenolane lactone of the formula:

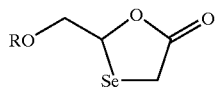

wherein R is hydrogen, acyl, a mono-, di- or triphosphate ester, or an ether lipid, or a pharmaceutically acceptable salt thereof, comprising:
   (a) preparing a selenol dimer of the formula $(SeCH_2COOH)_2$;

(b) reducing said dimer; and
(c) coupling the reduction product with $ROCH_2CHO$ to form the 1,3-oxaselenolane lactone.

3. The process of claim 2, wherein $ROCH_2CHO$ is $BzOCH_2CHO$.

4. The process of claim 2, wherein the reduction and coupling are achieved without isolating any intermediates.

5. The process of any one of claims 2–4, wherein the reduction is achieved using $H_3PO_2$.

6. The process of claim 2, wherein the selenol dimer is prepared from a selenyl cyanide comprising:
   (a) coupling a selenyl cyanide of the formula KSeCN with $Br—CH_2CO_2Et$ to form $NCSeCH_2CO_2Et$;
   (b) dimerizing $NCSeCH_2CO_2Et$ to form $(SeCH_2CO_2Et)_2$; and if necessary
   (c) activating $(SeCH_2CO_2Et)_2$ to form $(SeCH_2CO_2H)_2$.

7. A process for preparing a 1,3-oxaselenolane nucleoside of the formula:

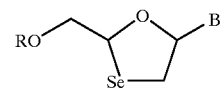

wherein B is a purine or pyrimidine base, and R is hydrogen, acyl, a mono-, di- or triphosphate ester, or an ether lipid, or a pharmaceutically acceptable salt thereof, comprising:
   (a) preparing a 1,3-oxaselenolane lactone of formula:

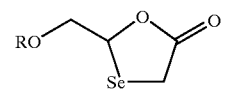

(b) activating said lactone to a compound of the formula:

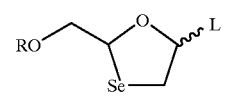

wherein L is an appropriate leaving group, halogen or acyl;
   (c) coupling the activated lactone with an optionally silylated base to form a 1,3-oxaselenolane nucleoside; and if necessary
   (d) deprotecting said nucleoside to form a 1,3-oxaselenolane nucleoside of the x formula:

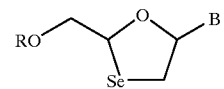

wherein B is a purine or pyrimidine base, and R is hydrogen; and optionally
   (e) activating said nucleoside to form a 1,3-oxaselenolane nucleoside of the formula:

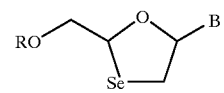

wherein B is a purine or pyrimidine base, and R acyl, a mono-, di- or triphosphate ester, or an ether lipid, or a pharmaceutically acceptable salt thereof.

8. The process of claim 7, wherein the coupling is achieved in the presence of trimethylsilyltriflate.

9. The process of claim 7, wherein L is acyl.

10. The process of claim 9 wherein L is acetyl.

11. The process of claim 9 or 10, wherein the activated lactone is prepared from the lactone comprising:

(a) reducing the lactone with a reducing agent to form an alcohol of the formula:

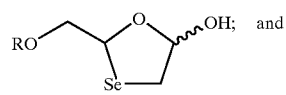 and (b) activating the alcohol to form the activated compound of the formula:

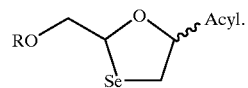

12. The process of claim 10, wherein the reducing agent is DIBAL-H.

13. The process of claim 10, wherein the activation of the alcohol is achieved with acetic anhydride.

* * * * *